(12) United States Patent
Morimitsu et al.

(10) Patent No.: US 7,998,266 B2
(45) Date of Patent: Aug. 16, 2011

(54) COLORED METALLIC PIGMENT, PROCESS FOR PRODUCING THE SAME, AND COATING COMPOSITION AND COSMETIC PREPARATION CONTAINING SAID COLORED METALLIC PIGMENT

(75) Inventors: Taro Morimitsu, Osaka (JP); Takayuki Nakao, Osaka (JP); Yoshiki Hashizume, Osaka (JP); Hideaki Minamiyama, Osaka (JP); Masakazu Nakamura, Osaka (JP)

(73) Assignee: Toyo Aluminium Kabushiki Kaisha, Osaka (JP)

( * ) Notice: Subject to any disclaimer, the term of this patent is extended or adjusted under 35 U.S.C. 154(b) by 552 days.

(21) Appl. No.: 12/279,306

(22) PCT Filed: Feb. 9, 2007

(86) PCT No.: PCT/JP2007/052338
§ 371 (c)(1),
(2), (4) Date: Aug. 13, 2008

(87) PCT Pub. No.: WO2007/094253
PCT Pub. Date: Aug. 23, 2007

(65) Prior Publication Data
US 2009/0017082 A1    Jan. 15, 2009

(30) Foreign Application Priority Data

Feb. 14, 2006 (JP) ................... 2006-036379

(51) Int. Cl.
*C04B 14/04* (2006.01)
*C04B 9/02* (2006.01)
*B05D 1/36* (2006.01)
*B32B 5/16* (2006.01)

(52) U.S. Cl. ............ 106/481; 106/14.05; 106/480; 106/483; 106/479; 427/205; 428/403; 428/546

(58) Field of Classification Search ............ 106/14.05, 106/479, 480, 481, 482–483, 491; 428/323, 428/328, 403–404, 546, 557, 823.2; 427/205; 424/401

See application file for complete search history.

(56) References Cited

U.S. PATENT DOCUMENTS

| | | | |
|---|---|---|---|
| 4,328,042 A | 5/1982 | Ostertag et al. | |
| 4,375,373 A * | 3/1983 | Abe et al. | 106/403 |
| 4,978,394 A | 12/1990 | Ostertag et al. | |
| 5,364,467 A | 11/1994 | Schmid et al. | |
| 5,607,504 A | 3/1997 | Schmid et al. | |
| 6,776,835 B2 * | 8/2004 | Andes et al. | 106/415 |
| 2003/0005859 A1 * | 1/2003 | Andes et al. | 106/403 |
| 2003/0209169 A1 | 11/2003 | Andes et al. | |
| 2004/0219344 A1 | 11/2004 | Andes et al. | |
| 2005/0147821 A1 | 7/2005 | Hashizume et al. | |

FOREIGN PATENT DOCUMENTS

| | | |
|---|---|---|
| EP | 0668329 A2 | 8/1995 |
| EP | 0741170 A1 | 11/1996 |
| EP | 1514907 A1 | 3/2005 |
| JP | 56-120771 A | 9/1981 |
| JP | 63-54475 A | 3/1988 |
| JP | 1-110568 A | 4/1989 |
| JP | 1-311176 A | 12/1989 |
| JP | 2-669 A | 1/1990 |
| JP | 6-32994 A | 2/1994 |
| JP | 7-258579 A | 10/1995 |
| JP | 8-209024 A | 8/1996 |
| JP | 9-59532 A | 3/1997 |
| JP | 9-328629 A | 12/1997 |
| JP | 10-81837 A | 3/1998 |
| JP | 2002-522618 A | 7/2002 |
| JP | 2003-41150 A | 2/2003 |
| JP | 2003-49093 A | 2/2003 |
| JP | 2003-89758 A | 3/2003 |
| JP | 2003-14722 A | 5/2003 |
| JP | 2003-131029 A | 5/2003 |
| JP | 2003-292825 A | 10/2003 |
| WO | WO-03/014228 A1 | 2/2003 |

* cited by examiner

*Primary Examiner* — Anthony J Green
*Assistant Examiner* — Pegah Parvini
(74) *Attorney, Agent, or Firm* — Birch, Stewart, Kolasch & Birch LLP

(57) ABSTRACT

This invention provides a colored metallic pigment, which can develop a variety of colors and varied interference colors while maintaining good lightfastness, weatherfastness and hiding power, a process for producing the same, a coating composition containing the colored metallic pigment and capable of providing a coating film having excellent finished appearance, and a cosmetic preparation containing the colored metallic pigment, having excellent hiding power, and capable of providing sharp hue. The colored metallic pigment comprises at least a metallic pigment, an amorphous silicon oxide film layer provided on the surface of the metallic pigment, a metal layer provided on the surface of the amorphous silicon oxide film layer, and metallic particles provided on the surface of the metal layer. The metallic particles are provided so as to directly cover a part of the surface of the metal layer. In the colored metallic pigment, the metal layer preferably comprises at least one metal selected from Sn, Pd, Pt and Au. The metallic particle preferably comprises at least one metal selected from Cu, Ni and Ag.

17 Claims, 3 Drawing Sheets

COLORED METALLIC PIGMENT, PROCESS FOR PRODUCING THE SAME, AND COATING COMPOSITION AND COSMETIC PREPARATION CONTAINING SAID COLORED METALLIC PIGMENT

TECHNICAL FIELD

The present invention relates to a colored metallic pigment excellent in finished appearance and a process for producing the same, as well as a coating composition and a cosmetic preparation containing the same.

BACKGROUND ART

As a colored metallic pigment having metallic effect excellent in Aesthetic effect, a pigment obtained by bonding a colored pigment to a metallic pigment is known in general. In this colored metallic pigment, an organic pigment such as a diketopyrrolopyrrole-based, quinacridone-based, dioxazine-based, isoindolinone-based, condensed azo-based, threne-based, perynone-based, perylene-based, phthalone-based or phthalocyanine-based pigment or an inorganic pigment such as iron oxide or carbon black is used as the colored pigment bonded to the metallic pigment.

In the aforementioned colored metallic pigment, however, the colored pigment bonded to the surface is disadvantageously easily photo-deteriorated due to optical reflection on the surface of the metallic pigment. In order to solve this problem, a pigment such as phthalocyanine blue, phthalocyanine green or iron oxide having relatively excellent light resistance must be selected, and the Aesthetic effect of the obtained colored metallic pigment is limited in the present circumstances.

In relation to a pearly pigment such as mica, on the other hand, a pigment supplied with interference colors by forming a film of silicon oxide, titanium oxide or metal on the surface is well known. However, the hiding power of such a pearly pigment is so small that an underlayer cannot be sufficiently covered even if the same is blended into paint or ink. While a metallic pigment covered with an interference film of silicon oxide, aluminum oxide or titanium oxide to be colored is disclosed as a metallic pigment having high hiding power in order to avoid this disadvantage, none is sufficient as the solving means.

Each of Japanese Patent Laying-Open No. 1-110568 (Patent Document 1) and Japanese Patent Laying-Open No. 2-669 (Patent Document 2) discloses a method of depositing titanium oxide on the surface of a metallic pigment by a sol-gel process. According to this method, however, no metallic pigment having high chroma can be obtained, and the titanium oxide layer may form a highly active anatase phase, to prompt degradation of resin and reduce weather resistance when blended into paint or the like.

Each of Japanese Patent Laying-Open No. 56-120771 (Patent Document 3), Japanese Patent Laying-Open No. 1-311176 (Patent Document 4) and Japanese Patent Laying-Open No. 6-32994 (Patent Document 5) discloses a method of forming a composite phase of iron oxide, titanium oxide and a metallic oxide and carbon, metal and a metallic oxide on the surface of a metallic pigment by a vapor phase process. When the vapor phase process is employed, however, the metallic pigment must be fluidized for supplying a precursor of the metallic oxide and heat-depositing the same on the surface of the metallic pigment. This deposition requires a specific apparatus and is extremely in danger of dust explosion of the metallic pigment, and the precursor of the metallic oxide is generally hard to handle due to strong toxicity.

Japanese Patent Laying-Open No. 8-209024 (Patent Document 6) discloses a multicoated metallic pigment based on a two-layer structure of a colorless coating layer having a refractive index of not more than 1.8 and a selective absorption layer having a refractive index of at least 2.0. Japanese Patent Laying-Open No. 8-209024 (Patent Document 6) also discloses a method of forming a metallic oxide layer on the surface of the metallic pigment by CVD (chemical vapor deposition) or by hydrolyzing a metallic compound in a solution. However, CVD has the aforementioned disadvantage. In the method of forming the metallic oxide layer by hydrolyzing the metallic compound in the solution, hydrolytic reaction is performed in a basic or acidic atmosphere containing a large quantity of water, and hence the metallic pigment reacts with water in the treatment step to result in a problem such as aggregation of the metallic pigment or runaway of the reaction.

Japanese Patent Laying-Open No. 7-258579 (Patent Document 7) discloses a luster pigment prepared by coating a substrate of aluminum flakes or the like with a multilayer film formed by a first layer consisting of silicon oxide, a silicon oxide hydrate, aluminum oxide and an aluminum oxide hydrate, a second layer consisting of metal and/or a nonselective absorption type metallic oxide and a third layer consisting of a colorless or selective absorption type metallic oxide at desire.

In the method disclosed in Japanese Patent Laying-Open No. 7-258579 (Patent Document 7), however, the thickness of the first layer tends to be nonuniform, and excellent chroma cannot be obtained. Further, the metallic oxides are not deposited on the surface of a substrate but tend to be liberated when the first layer is formed, reflected light is scattered by the liberated metallic oxide particles, and excellent metallic luster cannot be obtained. Further, while CVD and electroless plating are disclosed as methods of forming a metal layer on the first layer, CVD is dangerous and it is so difficult to homogeneously deposit the metal layer that particles not bonded with the metal are generally formed. Also in electroless plating, it is so difficult to finely and homogeneously deposit the metal layer that the metal layer is heterogeneously deposited in a scattered manner, and hence no preferable chroma can be obtained.

Japanese Patent Laying-Open No. 2003-49093 (Patent Document 8) discloses a multilayer luster pigment including a metallic base and a plurality of layers each completely enclosing the base, including at least one layer pack consisting of a colorless dielectric layer of a material having a refractive index of not more than 1.8 and another colorless dielectric layer of a material having a refractive index exceeding 1.8 and a selective or nonselective absorption layer. Japanese Patent Laying-Open No. 2003-131029 (Patent Document 9) discloses an optical multilayer system including a metal layer and a plurality of layers applied to both sides and one side thereof, including at least one layer pack consisting of a colorless dielectric layer of a material having a refractive index of not more than 1.8 and another colorless dielectric layer of a material having a refractive index exceeding 1.8 and a selective or nonselective absorption layer so that both of the layer pack and the selective or nonselective absorption layer do not completely enclose the metal layer. Japanese Patent Laying-Open No. 2003-89758 (Patent Document 10) discloses a high-saturation flaky pigment prepared by covering the overall surface of a metallic oxide-covered flaky substrate presenting interference colors due to the metallic oxide covering the same with a translucent metal thin film for strengthening the interference colors. Japanese Patent Laying-Open No. 2003-41150 (Patent Document 11) discloses a highly anticorrosive flaky metallic pigment having a coating layer comprising a metallic hydrate oxide of metal selected from a group consisting of silicon, aluminum, zirconium, titanium and tin on the surface of a flaky metallic substrate treated with a phosphoric acid compound and/or a boric acid compound. According to the method disclosed in each of Japanese Patent Laying-Open No. 2003-49093 (Patent Document 8), Japanese Patent Laying-Open No. 2003-131029 (Patent Document 9), Japanese Patent Laying-Open No. 2003-89758 (Patent Document 10) and Japanese Patent Laying-Open No. 2003-41150 (Patent Document 11), however, the degree of change of the interference colors or development of high chroma is limited, and it is disadvantageously difficult to obtain a colored metallic pigment having excellent Aesthetic effect of a satisfiable level.

Patent Document 1: Japanese Patent Laying-Open No. 1-110568
Patent Document 2: Japanese Patent Laying-Open No. 2-669
Patent Document 3: Japanese Patent Laying-Open No. 56-120771
Patent Document 4: Japanese Patent Laying-Open No. 1-311176
Patent Document 5: Japanese Patent Laying-Open No. 6-32994
Patent Document 6: Japanese Patent Laying-Open No. 8-209024
Patent Document 7: Japanese Patent Laying-Open No. 7-258579
Patent Document 8: Japanese Patent Laying-Open No. 2003-49093
Patent Document 9: Japanese Patent Laying-Open No. 2003-131029
Patent Document 10: Japanese Patent Laying-Open No. 2003-89758
Patent Document 11: Japanese Patent Laying-Open No. 2003-41150

DISCLOSURE OF THE INVENTION

Problems to be Solved by the Invention

An object of the present invention is to provide a colored metallic pigment capable of developing a variety of colors and varied interference colors while excellently maintaining light resistance, weather resistance and hiding power and a process for producing the same as well as a coating composition comprising the colored metallic pigment and capable of providing a coating film having excellent finished appearance and a cosmetic preparation comprising the colored metallic pigment, having excellent hiding power and capable of providing vivid hues, by solving the aforementioned problems.

Means for Solving the Problems

The present invention relates to a colored metallic pigment comprising at least a metallic pigment, an amorphous silicon oxide film layer provided on the surface of the metallic pigment, a metal layer provided on the surface of the amorphous silicon oxide film layer and metallic particles provided on the surface of the metal layer, in which the metallic particles are so provided as to directly cover part of the metal layer.

In the colored metallic pigment according to the present invention, the aforementioned metal layer preferably comprises at least one element selected from Sn, Pd, Pt and Au.

The metallic particles preferably comprise at least one element selected from Cu, Ni and Ag.

In the colored metallic pigment according to the present invention, an underlayer is preferably further formed between the metallic pigment and the amorphous silicon oxide film layer. This underlayer preferably consists of a single film or a mixture film of at least any one of an oxide, a hydroxide and a hydrate comprising molybdenum and/or phosphorus.

In the colored metallic pigment according to the present invention, a surface modification layer comprising an oxide of the metallic element constituting the metallic pigment is preferably formed on the surface of the metallic pigment.

In the colored metallic pigment according to the present invention, the thickness of the amorphous silicon oxide film layer is preferably in the range of 10 to 500 nm, and the average particle diameter of the metallic particles is preferably not more than 50 nm.

In the colored metallic pigment according to the present invention, a corrosion inhibiting layer consisting of a corrosion inhibitor is preferably formed on the metallic particles.

In the colored metallic pigment according to the present invention, a weather-resistant coating layer is preferably further formed on the metallic particles. This weather-resistant coating layer preferably consists of a single film or a mixture film of at least any one of an oxide, a hydroxide and a hydrate comprising at least one element selected from aluminum, silicon and cerium.

In the colored metallic pigment according to the present invention, a covering resin layer is preferably farther formed as the outermost layer.

The present invention also relates to a process for producing a colored metallic pigment, for obtaining the aforementioned colored metallic pigment, at least comprising an amorphous silicon oxide film layer forming step of forming an amorphous silicon oxide film layer on the surface of a metallic pigment by hydrolyzing an organic silicon compound in a solvent mainly composed of a hydrophilic solvent for depositing amorphous silicon oxide a metal layer forming step of depositing a metal layer on the surface of the amorphous silicon oxide film layer and a metallic particle forming step of forming metallic particles on the surface of the metal layer by electroless plating.

In the process for producing a colored metallic pigment according to the present invention, the aforementioned metal layer preferably comprises at least one element selected from Sn, Pd, Pt and Au.

The process for producing a colored metallic pigment according to the present invention preferably further comprises an underlayer forming step of performing pretreatment on the surface of the metallic pigment with inorganic acid comprising molybdenum and/or phosphorus for forming an underlayer consisting of a single film or a mixture film of at least any one of an oxide, a hydroxide and a hydrate comprising the molybdenum and/or the phosphorus in advance of the amorphous silicon oxide film layer forming step.

The process for producing a colored metallic pigment according to the present invention preferably further comprises a surface modification layer forming step of forming a surface modification layer comprising an oxide of the metallic element constituting the metallic pigment by treating the surface of the metallic pigment with hydrogen peroxide in advance of the amorphous silicon oxide film layer forming step.

The process for producing a colored metallic pigment according to the present invention preferably further comprises a corrosion inhibiting layer forming step of forming a corrosion inhibiting layer consisting of a corrosion inhibitor after the metallic particle forming step.

The process for producing a colored metallic pigment according to the present invention preferably further comprises a weather-resistant coating layer forming step of forming a weather-resistant coating layer consisting of a single film or a mixture film of at least any one of an oxides a hydroxide and a hydrate comprising at least one element selected from aluminum, silicon and cerium after the metallic particle forming step, and a coupling treatment step of treating the weather-resistant coating layer with a coupling agent comprising silicon and/or titanium.

The present invention also relates to a coating composition and a cosmetic preparation at least comprising the aforementioned colored metallic pigment or a colored metallic pigment obtained by the aforementioned process.

EFFECTS OF THE INVENTION

According to the present invention, a colored metallic pigment capable of developing a variety of colors and varied interference colors while excellently maintaining light resistance, weather resistance and hiding power can be obtained through relatively simple and low-priced means by at least forming an amorphous silicon oxide film layer, a metal layer and metallic particles on the surface of a metallic pigment. Further, a coating composition capable of providing a coating film having excellent finished appearance and a cosmetic preparation comprising the colored metallic pigment, having excellent hiding power and capable of obtaining vivid hues can be provided by employing the colored metallic pigment.

BEST MODES FOR CARRYING OUT THE INVENTION

Figure 1:
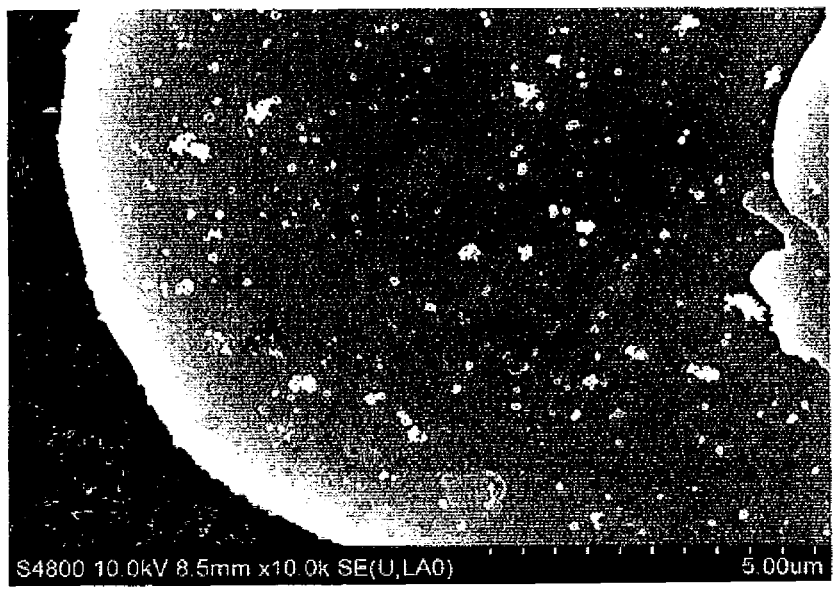
FIG. 1 shows the surface form of a colored aluminum pigment obtained in Example 2.

The colored metallic pigment according to the present invention is a colored metallic pigment comprising a metallic pigment, an amorphous silicon oxide film layer formed on the surface of the metallic pigment, a metal layer formed on the surface of the amorphous silicon oxide film layer and metallic particles formed on the surface of the metal layer. The colored metallic pigment according to the present invention is characterized in that the surface of the metal layer is only partially directly covered with the metallic particles. In other words, the metallic particles are not formed as a layer completely covering the base metallic pigment, whereby the colored metallic pigment according to the present invention has regions covered with the metallic particles and uncovered regions. The metallic particles are so formed as to partially cover the base metallic pigment, whereby only reflected light passing through the metallic particles is recognized as visible light in light reflected by the base metallic pigment. Consequently, it follows that brightness of the light reflected by the metallic pigment is weakened, and chroma, i.e., colors are developed. In the colored metallic pigment according to the present invention, further, interference colors having high chroma are developed by interference between the light reflected by the surface of the base metallic pigment and light reflected by the surfaces of the metallic particles.

According to the present invention, the metallic particles are so formed as to partially directly cover the metal layer, whereby exfoliation of the metallic particles is prevented by excellent adhesiveness between the metal layer and the metallic particles, and a colored metallic pigment developing a variety of colors and varied interference colors can be reliably obtained.

The colored metallic pigment according to the present invention is obtained by at least forming the amorphous silicon oxide film layer, the metal layer and the metallic particles on the surface of the metallic pigment, whereby the same can be produced through relatively simple means, and is advantageously supplied with excellent finished appearance without sacrificing light resistance, weather resistance and hiding power.

<Metallic Pigment>

For example, aluminum, copper, zinc, titanium, iron, nickel, chromium and an alloy thereof can be preferably illustrated as the metallic pigment used in the present invention, and aluminum is particularly preferably employed in the point of Aesthetic effect among these. When employing aluminum, for example, a multicolored metallic pigment presenting interference colors can be obtained by forming the amorphous silicon oxide film layer and further superposing the metallic particles.

The range of 2 to 300 μm can be illustrated as the preferable average particle diameter of the metallic pigment. A colored metallic pigment supplying excellent finished appearance and excellent hiding power to a coating film can be obtained if the average particle diameter is at least 2 μm, while a colored metallic pigment capable of preventing reduction of finished appearance of the coating film resulting from defective dispersion of the colored metallic pigment can be obtained if the average particle diameter is not more than 300 μm. The average particle diameter is further preferably set in the range of 5 to 100 μm. The average particle diameter of the metallic pigment in this specification means the average major axis.

The range of 0.01 to 5 μm can be illustrated as the preferable thickness of the metallic pigment. A colored metallic pigment capable of excellently maintaining finished appearance without damaging light resistance and weather resistance of the coating film is obtained if the thickness is at least 0.01 μm, while a colored metallic pigment supplying excellent Aesthetic effect and a variety of colors to the coating film can be obtained if the thickness is not more than 5 μm. The thickness is further preferably set in the range of 0.02 to 1 μm.

A flaky (i.e., scaly) shape having a ratio (A)/(B) between the average particle diameter (A) and the average thickness (B) in the range of 5 to 1000 can be preferably illustrated as the preferable shape of the metallic pigment. Aesthetic effect of the coating film is excellent and more various colors can be developed if the aforementioned ratio (A)/(B) is at least 5, while deformation of the metallic pigment in the process of producing the colored metallic pigment or reduction of dispersibility of the colored metallic pigment in the coating composition is preferably hardly caused if the ratio is not more than 1000. The ratio (A)/(B) is more preferably set in the range of 15 to 500. As the shape of the metallic pigment, a coin shape having a smooth surface and a rounded end surface is particularly preferable.

The metallic pigment used in the present invention is obtained as atomized powder or powder prepared by pulverizing metal flakes by wet ball milling (i.e., Hall process) or dry ball milling, for example. Alternatively, the metallic pigment is obtained by evaporating a metal thin film on a film or the like and thereafter separating/pulverizing The same.

<Amorphous Silicon Oxide Film Layer>

In the colored metallic pigment according to the present invention, the amorphous silicon oxide film layer is formed on the surface of the metallic pigment. While the amorphous silicon oxide film layer may be directly formed on the surface of the metallic pigment, another layer is preferably interposed between the metallic pigment and the amorphous silicon oxide film layer as an underlayer. While a layer consisting of a single film or a mixture film of at least any one of an oxide, a hydroxide and a hydrate comprising molybdenum and/or phosphorus as described later can be illustrated as the underlayer, the present invention is not restricted to this. One or at least two underlayers can be formed, and layers having different compositions may be stacked if at least two underlayers are formed.

In the present invention, a surface modification layer comprising an oxide of the metallic element constituting the metallic pigment as described later may be formed on the surface of the metallic pigment, so that this surface modification layer is interposed between the metallic pigment and the amorphous silicon oxide film layer. When the surface modification layer is formed in the present invention and the amorphous silicon oxide film layer is formed on this surface modification layer, the amorphous silicon oxide film advantageously easily grows from the surface modification layer.

In the present invention, either one of the surface modification layer and the underlayer may be formed, or both of the surface modification layer and the underlayer may be formed. When both of the surface modification layer and the underlayer are formed, the surface modification layer is formed on the surface of the metallic pigment and the underlayer is formed thereon, whereby adhesiveness between the metallic pigment and the underlayer is improved.

In the present invention, the amorphous silicon oxide film layer is so formed as to provide an arbitrary refractive index, thereby obtaining an effect of developing interference colors. As a method of forming the amorphous silicon oxide film layer, a method stirring or kneading the metallic pigment and a solution containing a silicon compound in a slurry state or a paste state while keeping the same basic or acidic, for example, can be employed, so that the amorphous silicon oxide film layer can be formed on the surface of the metallic pigment or the surface of the metallic pigment provided with the underlayer.

Methyltriethoxysilane, methyltrimethoxysilane, tetraethoxysilane, tetramethoxysilane, tetraisopropoxysilane or a condensate thereof, γ-aminopropyl triethoxysilane, N-2-aminoethyl-3-aminopropyl triethoxysilane, N-2-arninoethyl-3-aminopropylmethyl dimethoxysilane or the like can be illustrated as the aforementioned silicon compound.

A hydrophilic solvent such as methyl alcohol, ethyl alcohol, isopropyl alcohol, n-propyl alcohol, t-butyl alcohol, n-butyl alcohol, isobutyl alcohol, ethyl cellosolve, butyl cellosolve, propylene glycol monobutyl ether, dipropylene glycol monomethyl ether, propylene glycol monopropyl ether or acetone is preferably employed as the solvent for dissolving the silicon compound. Water sufficient for hydrolyzing alkoxysilane is desirably further blended into this solvent.

The thickness of the amorphous silicon oxide film layer is preferably set in the range of 10 to 500 nm, more preferably in the range of 10 to 100 nm. A coating film improving the state of adsorption of the metallic particles to the surface of the metallic pigment and presenting higher chroma can be formed if the thickness is at least 10 nm, while hiding power of the coating film is improved and danger of excessively damaging metallic appearance of the metallic pigment is small if the thickness is not more than 500 nm.

<Metal Layer>

In the present invention, the metal layer is formed on the surface of the amorphous silicon oxide film layer. This metal layer is so formed that interference colors having high chroma can be developed by densely and homogeneously depositing the metallic particles due to an excellent state of adsorption between the metallic particles and the metal layer. The metal layer preferably comprises at least one element selected from Sn (tin), Pd (palladium), Pt (platinum) and Au (gold), and particularly preferably comprises at least either one of Sn and Pd.

While the metal layer may be directly formed on the surface of the amorphous silicon oxide film layer, still another layer may be interposed between the amorphous silicon oxide film layer and the metal layer. A layer consisting of an oxide or a hydroxide of aluminum or cerium, for example, can be illustrated as this layer. While a method of depositing the metal layer is not particularly limited, a method of hydrolytically depositing metal alkoxide for forming the metal layer by a sol-gel process or a method of neutralizing/depositing the metal layer by adding alkali to a metallic salt solution containing the metal for forming the metal layer is suitable, for example. When forming the metallic particles by electroless plating, water-soluble metallic salt containing the metal for forming the metal layer is preferably used.

Tetraethoxytin or the like can be illustrated as the metal alkoxide used in the hydrolytically depositing method, and a colloidal solution in which the metal alkoxide is dispersed can be preferably used. Ammonia water, ethylenediamine, monoethanol amine, diethanol amine, hydrazine, urea or the like can be illustrated as the hydrolytic catalyst for the metal alkoxide.

Tin chloride, tin fluoride or the like can be illustrated as the metallic salt used in the neutralizing/depositing method. Ammonia water, sodium hydroxide, monoethanol amine, diethanol amine or the like can be illustrated as a neutralizer for the metallic salt. Water, ethanol, isopropyl alcohol, methylpropylene glycol, butyl cellosolve or the like can be illustrated as a reactive solvent.

When the metallic particles in the present invention are formed by electroless plating with water-soluble metallic salt, the metal layer can be formed by a method employed as pretreatment for the electrolytic plating. The pretreatment for the electrolytic plating generally includes the catalyst (also referred to as catalyzing)-accelerator (also referred to as accelerating) process and the sensitizing-activating process, and either process may be employed. Further, only the catalyst process or the sensitizing process may be performed.

The catalyst-accelerator process is a method employing a mixed solution containing Sn and any one of Pd, Pt and Au as a catalyst, dipping the metallic pigment provided with the amorphous silicon oxide film layer in this catalyst, adsorbing a complex compound of any one of Pd, Pt and Au and Sn to the surface of the metallic pigment, thereafter employing an acidic solution such as sulfuric acid or hydrochloric acid or an alkaline solution such as sodium hydroxide or ammonia as an accelerator, dipping the aforementioned metallic pigment in this accelerator, removing Sn and activating any of Pd, Pt and Au.

The sensitizing-activating process is a method employing an Sn solution as a sensitizing solution, dipping the metallic pigment provided with the amorphous silicon oxide film layer in this sensitizing solution, adsorbing Sn to the surface of the metallic pigment, thereafter employing a solution containing any one of Pd, Pt and Au as an activating solution and carrying any one of Pd, Pt and Au on the surface of the aforementioned metallic pigment.

The sensitizing process is a method employing an Sn solution as a sensitizing solution and dipping the metallic pigment provided with the amorphous silicon oxide film layer in this sensitizing solution for adsorbing Sn to the surface of the metallic pigment, thereby carrying Sn on the surface of the metallic pigment.

Water-soluble metallic salt containing any one of Sn, Pd, Pt and Au can be used as a metal source for the metal layer formed in the method employed as the pretreatment for the electroless plating. Tin chloride, tin oxalate, tin sulfate, tin bromide, tin acetate, tin borofluoride, tin fluoride, sodium stannate, potassium stannate, tin mesylate, tin sulfide, tin silicofluoride, palladium chloride, palladium acetate, palladium bromide, palladium hydroxide, palladium nitrate, palladium oxide, palladium sulfate, gold bromide, gold chloride, platinum chloride, platinum oxide or the like can be illustrated as specific metallic salt.

According to the aforementioned method, a catalyst layer of Sn, Pd, Pt, Au or the like is carried as the metal layer in the present invention. Thereafter the metallic particles can be formed on the surface of this metal layer by electroless plating. When the metallic pigment provided with the metal layer is dipped in an electroless plating solution, a reducing agent in the plating solution is oxidized on the surface of the metal layer due to catalytic activity of the metal layer. Metallic ions in the electroless plating solution are reduced by electrons emitted at this time, the metal is deposited on the surface of the metal layer, and the metallic particles are formed.

In the present invention, the thickness of the metal layer is preferably set to not more than 30 nm. In this case, more excellent chroma and interference colors are provided by the obtained colored metallic pigment. The thickness of the metal layer is farther preferably set in the range of 0.1 to 10 nm. The thickness of the metal layer can be confirmed as the layer of metal formed between the amorphous silicon oxide film layer and the metallic particles in high magnification observation of about 3 million magnifications in a transmission electron microscope (TEM), for example. Presence of the element can also be confirmed by local EDS (energy-dispersive X-ray spectroscopy). The metal layer is typically formed by a continuous layer of aggregates of particles.

The metal layer may be homogeneously deposited or heterogeneously deposited on the surface of the amorphous silicon film layer. Even if the thickness of the metal layer is so small that the same cannot be observed with a TEM, for example, the metallic particles call be densely and homogeneously deposited when the metal layer is deposited.

<Metallic Particles>

In the colored metallic pigment according to the present invention, the metallic particles are so deposited as to partially directly cover the surface of the metal layer. The colored metallic pigment according to the present invention has regions where no metallic particles are formed, i.e., regions not covered with the metallic particles. Thus, interference is caused between light reflected by the surfaces of the metallic particles and light reflected by the surface of the base metallic pigment to pass through the amorphous silicon oxide film layer, whereby a colored metallic pigment presenting interference colors having high chroma is obtained. Further, the metallic particles are so directly formed on the surface of the metal layer that adhesiveness between the metal layer and the metallic particles is improved, and a colored metallic pigment having a variety of colors and varied interference colors can be reliably obtained.

For example, particles comprising at least one element selected from Al (aluminum), Ti (titanium), Cr (chromium), Fe (iron), Co (cobalt), Ni (nickel), Cu (copper), Zn (zinc), Ru (ruthenium), Rh (rhodium), Pd (palladium), Ag (silver), Sn (tin), Pt (platinum), Au (gold) and alloys thereof can be preferably illustrated as the material for the metallic particles in the present invention. When the metallic particles comprise at least one element selected from these metals and metal alloys, a colored metallic pigment presenting interference colors having high chroma is obtained. Particles comprising at least one element selected from Cu, Ni and Ag can be listed as particularly preferable particles.

The average particle diameter of the metallic particles is preferably set to not more than 50 nm. In this case, the surface form of the surface of the colored metallic pigment having regions provided with the metallic particles and regions not provided with the metallic particles is relatively smooth, and a colored metallic pigment capable of providing a metallic film excellent in finished appearance is obtained. The average particle diameter of the metallic particles is more preferably set to not more than 30 nm.

In the colored metallic pigment according to the present invention, further, it is particularly preferable that the thickness of the amorphous silicon oxide film layer is in the range of 10 to 500 nm and the average particle diameter of the metallic particles is not more than 50 nm. In this case, interference colors having particularly high chroma are developed.

While the metallic particles formed in the colored metallic pigment according to the present invention are so formed as not to completely cover the metal layer but to partially cover the metal layer, the interval between the metallic particles is preferably set to not more than 10 nm, in a point that a colored metallic pigment having higher chroma is obtained. In the present invention, at least two metallic particles may be deposited on the metal layer in a superposed manner, while the metallic particles are preferably deposited as single particles in a single-layered manner. In this case, light is scattered in the amorphous silicon oxide film layer due to the light reflected by the base metallic pigment and the light reflected by the metallic particles, and interference colors having high chroma are provided by interference of the reflected light passing through the metallic particles. Further, the respective metallic particles are preferably deposited on the metal layer without coming into contact with each other. Most typically, the respective metallic particles are preferably deposited on the metal layer in a single-layered manner without coming into contact with each other so that the interval between the metallic particles is not more than 10 nm.

The deposited state of the metallic particles, the average particle diameter thereof and the interval between the metallic particles can be evaluated by sectional observation with a transmission electron microscope (TEM), for example. In this case, a method of performing FIB (focused ion beam) working on a section of the colored metallic pigment provided with the metallic particles can be preferably employed for preparing a sample for observation. According to this method, the worked portion can be decided while observing a scanning ion microscopy (SIM) image, whereby a specific portion in the sample can be worked. Working is performed by the aforementioned method, for observing sections of the metallic particles with a transmission electron microscope (TEM) at 30 to 3 million magnifications.

While the method of forming the metallic particles is not particularly limited, vacuum evaporation, sputtering, chemical vapor deposition, electroless plating or the like is suitable. Among these methods, electroless plating capable of homogeneously depositing the metallic particles and obtaining excellent chroma is particularly suitable.

When employing chemical vapor deposition, the metallic particles can be deposited by directly introducing iron oxide or the like onto the surface of the metal layer by a well-known method described in Japanese Patent Laying-Open No. 56-120771, Japanese Patent Laying-Open No. 1-311176 or Japanese Patent Laying-Open No. 6-32994, for example.

<Underlayer>

In the present invention, an underlayer, particularly an underlayer comprising molybdenum and/or phosphorus is preferably further formed between the metallic pigment and the amorphous silicon oxide film layer. This underlayer is so formed that the amorphous silicon oxide film layer formed thereon can be more homogeneously deposited. Thus, the thickness of the amorphous silicon oxide film layer is rendered uniform, and a colored metallic pigment presenting interference colors having higher chroma can be obtained. The underlayer comprising molybdenum and/or phosphorus has excellent corrosion resistance, whereby an effect of preventing abnormal reaction between the treatment solution and the metallic pigment in the step of forming the amorphous silicon oxide film layer is also attained by forming this underlayer.

While the method of forming the underlayer comprising molybdenum and/or phosphorus on the surface of the metallic pigment is not particularly limited, a method stirring or kneading the metallic pigment and a solution containing a molybdenum compound and/or a phosphorus compound in a slurry state or a paste state thereby forming a hydrate film containing molybdenum and/or phosphorus on the surface of the metallic pigment and thereafter forming an oxide film by heating is illustrated as a preferable method. As to the details of the method of forming the underlayer, the well-known method disclosed in Japanese Patent Laying-Open No. 9-328629, Japanese Patent Laying-Open No. 63-054475 or the like can be employed.

Peroxidic polymolybdic acid expressed in a composition formula $Mo_xO_y \cdot mH_2O_2 \cdot nH_2O$ (where x represents 1 or 2, y represents an integer of 2 to 5, and m and n represent arbitrary positive numbers), ammonium molybdate, phosphomolybdic acid or the like is illustrated as the molybdenum compound employed for forming the underlayer. Peroxidic polymolybdic acid can be prepared by dissolving metal molybdenum powder or molybdenum oxide into an aqueous hydrogen peroxide solution (concentration: 5 to 40 mass %). This compound is dissolved in a hydrophilic solvent such as methyl alcohol, ethyl alcohol, isopropyl alcohol, n-propyl alcohol, t-butyl alcohol, n-butyl alcohol, isobutyl alcohol, ethyl cellosolve, butyl cellosolve, propylene glycol monobutyl ether, dipropylene glycol monomethyl ether, propylene glycol monopropyl ether, acetone or the like for preparing the treatment solution. The treatment solution may contain water.

Normal phosphoric acid, phosphorous acid, hydrophosphorous acid, phosphinic acid, pyrophosphoric acid, polyphosphoric acid or the like is illustrated as the phosphorus compound employed for forming the underlayer. This compound is dissolved in a hydrophilic solvent such as methyl alcohol, ethyl alcohol, isopropyl alcohol, n-propyl alcohol, t-butyl alcohol, n-butyl alcohol, isobutyl alcohol, ethyl cellosolve, butyl cellosolve, propylene glycol monobutyl ether, dipropylene glycol monomethyl ether, propylene glycol monopropyl ether, acetone or the like for preparing the treatment solution. The treatment solution may contain water.

The quantity of molybdenum and/or phosphorus in the underlayer is preferably 0.01 to 3.0 parts by mass, more preferably 0.05 to 2.0 parts by mass with respect to 100 parts by mass of the metallic pigment. The quantity of molybdenum and/or phosphorus is desirably varied with the specific surface area of the treated metallic pigment. The quantity of molybdenum and/or phosphorus is preferably increased with respect to a metallic pigment having a large specific surface area and reduced if the specific surface area is small. Uniformity of the thickness of the amorphous silicon oxide film layer and chemical stability of the metallic pigment in formation of the amorphous silicon oxide film layer are excellent if the quantity of molybdenum and/or phosphorus is at least 0.01 parts by mass with respect to 100 parts by mass of the metallic pigment, while reduction in the tone such as metallic luster, for example, of the metallic pigment and aggregation of the metallic pigment are prevented and film properties such as moisture resistance, adhesiveness and weather resistance are excellently maintained if the quantity is not more than 3.0 parts by mass.

The thickness of the underlayer is preferably set in the range of 0.5 to 10 nm. Uniformity of the thickness of the amorphous silicon oxide film layer and chemical stability of the metallic pigment in formation of the amorphous silicon oxide film layer are excellent if the thickness of the underlayer is at least 0.5 nm, while reduction in the tone such as metallic luster, for example, of the metallic pigment and aggregation of the metallic pigment are prevented and film properties such as moisture resistance, adhesiveness and weather resistance are excellently maintained if the thickness is not more than 10 nm.

<Surface Modification Layer>

In the present invention, a surface modification layer comprising an oxide of the metallic element constituting the metallic pigment is preferably formed on the surface of the metallic pigment. When forming such a surface modification layer and forming the amorphous silicon oxide film layer thereon, the surface of the metallic pigment is modified to a state easily growing the amorphous silicon oxide film layer by the surface modification layer, whereby a more homogeneous amorphous silicon oxide film layer can be formed and a colored metallic pigment presenting interference colors having higher chroma can be obtained.

The surface modification layer is typically formed by treating the surface of the metallic pigment with hydrogen peroxide. The surface of the metallic pigment is so treated with hydrogen peroxide that aliphatic acid adsorbed to the surface of the metallic pigment is removed, the surface of the metallic pigment is oxidized and the surface modification layer comprising the oxide of the metallic element constituting the metallic pigment is formed. Thus, the surface of the metallic pigment is modified to the surface state easily growing the amorphous silicon oxide film layer from the surface modification layer.

While the method of forming the surface modification layer on the surface of the metallic pigment is not particularly limited, a method stirring or kneading the metallic pigment and a solution containing hydrogen peroxide in a slurry state or a paste state thereby forming a hydrate film comprising the metallic element constituting the metallic pigment on the surface of the metallic pigment and thereafter converting the hydrate film to an oxide film by heating or the like can be illustrated as a preferable method.

When using an aluminum pigment as the metallic pigment and stirring or kneading this aluminum pigment and a solution containing hydrogen peroxide in a slurry state or a paste state, for example, a hydrate film comprising aluminum is formed on the surface of the aluminum pigment, and an oxide film such as an aluminum oxide film or a boehmite film is formed by heating.

A solution prepared by dissolving hydrogen peroxide in a solvent can be typically used as the solution containing hydrogen peroxide. Alcohol, glycol, glycol ether, a ketonic organic solvent or the like can be used as the solvent in addition to water, and a mixed solvent of water and an organic solvent or the like can also be used. The hydrogen peroxide concentration in the solution is preferably in the range of 0.0001 to 45 mass %.

The thickness of the surface modification layer is preferably set in the range of 0.5 to 10 nm. Uniformity of the thickness of the amorphous silicon oxide film layer and chemical stability of the metallic pigment in formation of the amorphous silicon oxide film layer are excellent if the thickness of the surface modification layer is at least 0.5 nm, while reduction in the tone such as metallic luster, for example, of the metallic pigment and aggregation of the metallic pigment are prevented and film properties such as moisture resistance, adhesiveness and weather resistance are excellent if the thickness is not more than 10 nm. The thickness of the surface modification layer is more preferably at least 1 nm, and further preferably not more than 5 nm. The thickness of the surface modification layer can be confirmed by ESCA (Electron Spectroscopy for Chemical Analysis). Measurement of an oxide film by ESCA can be performed as follows, for example; In other words, "SSX-100" by SSI, U.S.A. is employed, and a single-crystal spectral A1Kα radiation is employed as an X-ray source. The thickness of the oxide film is measured up to a depth of about 63 nm (in terms of $SiO_2$) from the outermost surface of the sample through depth profile analysis by Ar ion etching. The measurement is performed with detection angle inclination of 35° with respect to the surface of the sample. Such a depth that the ratio ($AlO_x$/$Al^0$) between the metal aluminum component ($Al^0$) and the oxide component ($AlO_x$) of an Al2p peak is not more than 1 is calculated from the result of the depth profile as the thickness of the oxide film (in terms of $SiO_2$).

<Corrosion Inhibiting Layer>

In the colored metallic pigment according to the present invention, a corrosion inhibiting layer consisting of a corrosion inhibitor is preferably formed on the metallic particles. While the corrosion inhibiting layer may contain a substance having a corrosion inhibiting function with respect to the metallic particles, a corrosion inhibiting layer consisting of a single film comprising at least either one of an organic compound having a corrosion inhibiting function with respect to the metal and a surface active agent having a corrosion inhibiting function with respect to the metal or a mixture film comprising at least two of the aforementioned organic compound and the surface active agent is typically preferably formed.

When metal such as silver or copper which oxidize or sulfurize easily is used as the material for the metallic particles, weather resistance is effectively provided by forming the corrosion inhibiting layer.

While the method of forming the corrosion inhibiting layer is not particularly limited, a method adding a corrosion inhibitor to a suspension of a slurry state or a paste state prepared by suspending the metallic pigment at least provided with the metallic particles in a hydrophilic solvent and stirring or kneading the mixture thereby bonding the corrosion inhibitor to the surface of the aforementioned metallic pigment is preferably employed.

While any well-known discoloration inhibitor can be used as the corrosion inhibitor, benzotriazoles such as benzotriazole, 1-methylbenzotriazole, 4-methylbenzotriazole, 1-ethylbenzotriazole, 1-hydroxybenzotriazole, 4-carboxybenzotriazole, 1-chlorbenzotriazole, 5-chlorbenzotriazole, N-acetyl-benzotriazole, N-butyryl-benzotriazole, N-pivaloyl-benzotriazole, N-nonanoyl-benzotriazole, N-caproyl-benzotriazole, N-caprylyl-benzotriazole, N-lauroyl-benzotriazole, N-stearyl-benzotriazole, N-oleoyl-benzotriazole, naphthotriazole, tolyltriazole, 2-(2'-hydroxy-5'-methylphenyl) benzotriazoic, 2-(2'-hydroxy-3,5'-di-tert-butylphenyt) benzotriazole, (di)ethylaminomethyl benzotriazole, (di)butylaminomethyl benzotriazole, (di)octylaminomethyl benzotriazole, (di)tridecylaminomethyl benzotriazole, (di)octadecylaminomethyl benzotriazole, (di)cyclohexylaminomethyl benzotriazole, (di)allylaminomethyl benzotriazole, (di)benzylaminomethyl benzotriazole, (di)octylaminoethyl benzotriazole, (di)octylaminodecyl benzotriazole and (di)octylaminobenzyl benzotriazole, tetrazoles such as 1-phenyl-5-mercaptotetrazole, 3-(4,5dimethyl-2-thiazolyl)-2,5-diphenyl2H-tetrazolium bromide and 5-amino-1H-tetrazole, imidazoles such as 2-phenylimidazole, 2-phenyl-4-methylimidazole, 2-phenyl-4-propylimidazole, 2-phenyl-5-iodoimidazole, 2-benzylimidazole, 2-benzyl-4-methylimidazole, 2-(3-chlor)benzylimidazole, 2-(3-iodo)benzylimidazole, 2-naphthylimidazole, 2-naphtyl-4-methylimidazole, 2-naphtyl-4-methyl-5-bromimidazole, 2-(3,5-dibrom)naphtylimidazote, 2-(2,6-dichlor)naphtyl-4-methylimidazole, 2-mercaptobenzoimidazole, 2-mercaptomethyl benzoicmidazole, 2-amylimidazole, 2-heptylimidazole, 2-decylimidazole, 2-undecylimidazole, 2-dodecylimidazole, 2-tridecylimidazole, 2-tetradecylimidazole. 2-heptadecylimidazole, 2-undecyl-4-methylimidazole and 2-heptadecyl-4-methylimidazole, allcylamino triazoles such as 3-amino-1,2,4-triazole, 3-amino-S-methyl-1,2,4-triazole, 3-amino-5-ethyl-1,2,4-triazole, 3-amino-5-propyl-1,2,4-triazole, 3-amino-5-butyl-1,2,4-triazoie, 3-amino-5-pentyl-1,2,4-triazole, 3-amino-5-hexyl-1,2,4-triazole, 3-amino-5-heptyl-1,2,4-triazole, 3-amino-5-octyl-1,2,4-triazole, 3-amino-5-nonyl-1,2,4-triazole, 3-amino-5-decyl-1,2,4-triazole, 3-amino-5-undecyl-1,2,4-triazole and 3-amino-5-dodecyl-1,2,4-triazole, α- or β-dicarbonyl compounds such as glyoxal, pyi-voaldehyde, diacetyl, 2,3-pentanedione, 3,4-hexanedione, 3,4-heptanedione, 3,4-octanedione, 4,5-nonanedione, 4,5-decanedione, 5,6-undecanedione, 1,2-cyclohexanedione, acetylacetone, 2,4-hexanedione, 2,4-heptanedione, 2,4-octanedione, 3,5-octanedione, 4,6-decanedione, 5,7-undecanedione, methyl acetoacetate, ethyl acetoacetate, 3-methyl-2,4-pentanedione, 2-acetylcyclopentanone, α-acetyl-γ-butyrolactone, 2-ethylcarbonyl cyclopentanone, α-ethylcarbonyl-γ-butyrolactone, 2-propylcarbonyl cyclopentanone, α-propylcarbonyl-γ-butyrolactone, 2-butylcarbonyl cyclopentanone, α-butylcarbonyl-γ-butyrolactone, 2-acetylcyclohexanone, α-acetyl-δ-pentylolactone, 2-ethylcarbonyl cyclohexanone, α-ethylcarbonyl-γ-pentylolactone, 2-propylcarbonyl cyclohexanone, α-propylcarbonyl-γ-pentylolactone, 2-butylcarbonyl cyclohexanone and α-butylcarbonyl-γ-pentylolactone or amine adducts thereof and mercaptan compounds such as mercaptoimidazoline, naphtylmercaptan, alkylmercaptan of C6 to C22 can be listed as particularly preferably employed materials.

Further, higher alkylamines such as dodecylamine, octadecylamine, icosyl amine and nonyl amine and ethylene oxide adducts thereof can also be listed.

In addition, benzothiazoles such as 2-methylbenzothiazole, 2-mercaptobenzothiazole, 2-(4'-morpholinodithio) benzothiazole, N-cyclohexyl-2-benzothiazolyl sulfenamide, N-oxydiethylene-2-benzothiazolyl sulfenamide and N-tert-butyl-2-benzothiazolyl sulfenamide can also be listed.

While the content of the corrosion inhibitor is not particularly limited so far as the effects of the colored metallic pigment according to the present invention are not damaged, the corrosion inhibitor is preferably so employed that the content in 1 kg of the solution is generally in the range of 1 ppm to 5 mass %.

The corrosion inhibitor is preferably added to the aforementioned suspension along with a proper solvent. While the solvent is not particularly limited, water, methyl alcohol, ethyl alcohol, isopropyl alcohol, n-propyl alcohol, t-butyl alcohol, n-butyl alcohol, isobutyl alcohol, ethyl cellosolve, butyl cellosolve, propylene glycol monobutyl ether, propylene glycol monomethyl ether, propylene glycol monopropyl ether, ethylene glycol monoethyl ether, acetone or benzene can be listed.

The pH of the solution containing the corrosion inhibitor can be set in a wide range of pH 1 to pH 13, the effect of corrosion inhibition is sufficiently attained in the weak acid to weak base region, and hence the solution is desirably employed with pH 4 to pH 11 in view of safety. While well-known acid and/or alkali can be used when the pH is adjusted, hydrochloric acid or nitric acid may corrode the basis metal if it is employed in large quantity, and hence sulfuric acid or sulfonic acid is preferably employed as acid, and sodium hydroxide, potassium hydroxide or ammonia is preferably employed as alkali.

<Weather-Resistant Coating Layer>

In the present invention, a weather-resistant coating layer consisting of a single film or a mixture film of at least any one of an oxide, a hydroxide and a hydrate, particularly a weather-resistant coating layer consisting of a single film or a mixture film of at least any one of an oxide, a hydroxide and a hydrate comprising at least any one element selected from aluminum, silicon and cerium is preferably further formed on the metallic particles. The weather-resistant coating layer is so formed that a discoloration preventing effect is supplied to a film blended with the colored metallic pigment according to the present invention and weather resistance of the film can be improved. Particularly when metal such as silver or copper which oxidize or sulfurize easily is used as the material for the metallic particles, weather resistance is effectively supplied by forming the weather-resistant coating layer.

In a case of forming the aforementioned corrosion inhibiting layer on the metallic particles in the present invention, the weather-resistant coating layer is preferably formed on this corrosion inhibiting layer. In this case, the weather resistance effect in prolonged exposure is improved, and oxidation or sulfuration resulting from heating can be advantageously suppressed in particular.

While the method of forming the weather-resistant coating layer is not particularly limited, a method adding a silicon compound and/or an aluminum compound to a suspension of a slurry state or a paste state prepared by suspending the metallic pigment at least provided with the amorphous silicon oxide film layer and the metallic particles in a hydrophilic solvent and stirring or kneading the same while keeping the pH of the suspension basic or acidic thereby forming a hydrate film containing silicon and/or aluminum as the element(s) on the surface of the aforementioned metallic pigment and finally converting the hydrate film to a single film or a mixture film of at least any one of an oxide, a hydroxide and a hydrate by heat-treating the same at a high temperature is preferably employed when the weather-resistant coating layer comprises aluminum and/or silicon, for example. It is recommended to previously solid-liquid separate paste containing the metallic pigment having the hydrate film from the aforementioned suspension before the final beat treatment.

While the silicon compound and/or the aluminum compound employed in the aforementioned method is not particularly limited, methyl triethoxysilane, methyl trimethoxysilane, tetraethoxysilane, tetramethoxysilane or tetraitsoprop oxysilane or a condensate thereof, γ-aminopropyl triethoxysilane, N-2-arminoethyl-3-aminopropyl triethoxysilane, N-2-aminoethyl-3-aminopropyl methyl dimethoxysilane, sodium silicate, silicotungstic acid, silicomolybdic acid, triethoxy aluminum, trimethoxy aluminum or trilsopropoxy aluminum or a condensate thereof or aluminum nitrate can be listed.

While the hydrophilic solvent employed for the suspension in the aforementioned case is not particularly limited, methyl alcohol, ethyl alcohol, isopropyl alcohol, n-propyl alcohol, t-butyl alcohol, ni-butyl alcohol, isobutyl alcohol, ethyl cellosolve, butyl cellosolve, propylene glycol, monobutyl ether, dipropylene glycol monomethyl ether, propylene glycol monopropyl ether, acetone or the like can be listed. The aforementioned suspension may contain water.

When the weather-resistant coating layer comprises cerium, a method adding the metallic pigment at least provided with the amorphous silicon oxide film layer and the metallic particles to a solution in which cerium acetate, cerium nitrate, cerium alkoxide or cerium sol is dissolved or dispersed and heating/stirring or kneading the same while keeping a basic atmosphere can be preferably employed.

The thickness of the weather-resistant coating layer is preferably set in the range of 1 to 100 mm. Water resistance, heat resistance and weather resistance of a film formed with the colored metallic pigment according to the present invention are excellent if the thickness is at least 1 nm, while luster of the base metallic pigment is excellently developed in the film if the thickness is not more than 100 nm. The thickness of the weather-resistant coating layer is more preferably set in the range of 20 to 50 nm.

<Coupling Agent>

In the present invention, the weather-resistant coating layer is preferably further treated with a coupling agent, particularly a coupling agent comprising silicon and/or titanium when forming the metallic particles or the aforementioned weather-resistant coating layer. In this case, affinity between the colored metallic pigment and coating resin is improved when a film is prepared from a coating composition comprising the colored metallic pigment according to the present invention and the coating resin, whereby an effect of improving adhesiveness of the film is attained. For example, a silane coupling agent is preferable as the coupling agent. $R_A$—Si$(OR_B)_3$ or $R_A$—Si$R_B(OR_B)_2$ ($R_A$: alkcyl group or aryl group or alkenyl group having a carbon number of 2 to 18, $R_B$: alkyl group having a carbon number of 1 to 3) can be preferably illustrated as the silane coupling agent. It is also preferable that $R_A$ in the above formula has a functional group. An amino group, a ureido group, an epoxy group) a sulfide group, a vinyl group, a methacryloxy (methacrylic) group, an acryloxy (acrylic) group, a mercapto group or a ketimino group can be listed as the functional group.

Methyltriethoxysilane, methyltrimethoxysilane, tetraethoxysilane, tetrarmethoxysilane, tetraisopropoxysilane, 3-aminopropyl-trimethoxysilane, n-methyl-3-aminopropyl-trimethoxysilane, 3-atminopropyl-triethoxysilane, 3-aminopropyl-tris(2-methoxy-epoxy-silane), n-aminoethyl-3-aminopropyl trimethoxysilane, 3-methacryloxypropyl-trimethoxysilane, 3-acryloxypropyl-trimethoxysilane, 3-glycidyloxypropyl-triimethoxysilane, 3-mercaptopropyl-trimethoxysilane, 3-mercaptopropyl-triethoxysilane, 3-mercaptopropyl-methyldimethoxysilane, vinyltrichlorosilane, vinyltrimethoxysilane, vinyltriethoxysilane or vinyl-tris(2-methoxyethoxy) silane or a condensate thereof can be listed as a preferable specific example of an organic silicon compound employed as the silane coupling agent.

A titanium coupling agent, smaller in number of types as compared with the silane coupling agent, can be preferably employed as the coupling agent in the present invention. The titanium coupling agent generally has a hydrophilic hydrolyzable group and a hydrophobic side-chain organic functional group. Typically, an alkoxyl group is contained as the hydrophilic hydrolyzable group, and an alkylphophoric ester group, an amino group or a sulfide group is contained as the hydrophobic side-chain organic functional group. Prene Act KR46B by Ajinomoto Fine-Techno Co., Inc. or the like can be listed as an exemplary preferable commercially available product of the titanium coupling agent. For example, Prene Act KR46B has such a structure that $C_8H_{17}O-$ and $HO-P-(OC_{13}H_{27})_2$, $C_8H_{17}O-$ coordinate with Ti as the hydrolizable group and the side-chain organic functional group respectively.

When performing the coupling treatment) the content of the coupling agent is preferably set to be in the range of 0.1 to 30 mass % of the pigment before the coupling treatment. An effect of improving adhesiveness of the film is excellent if the content of the coupling agent is at least 0.1 mass % of the pigment before the coupling treatment, while age stability of the colored metallic pigment, particularly an effect of preventing aggregation is preferably excellent if the content is not more than 30 mass %. The content of the coupling agent is more preferably set in the range of 1 to 5 mass % of the pigment before the coupling treatment.

The coupling treatment can be performed by a method dispersing the metallic pigment provided with the metallic particles or the metallic pigment further provided with the weather-resistant coating layer on the metallic particles in a solvent such as isopropyl alcohol, slurrying the same and thereafter adding the coupling agent thereto or the like.

<Covering Resin Layer>

A covering resin layer is preferably formed on the colored metallic pigment according to the present invention as the outermost layer. When forming a film with the coating composition prepared by blending the colored metallic pigment according to the present invention and the coating resin, adhesiveness between the colored metallic pigment and the coating resin is improved and film properties are advantageously improved in this case. Further, chemical resistance of the film is also advantageously improved due to the formation of the covering resin layer.

While the method of forming the covering resin layer is not particularly limited, a method solid-liquid separating the metallic pigment provided with the metallic particles, cleaning/filtrating the same with a nonpolar solvent if necessary, thereafter dispersing the same in the nonpolar solvent, adding a polymerizable monomer and a polymerization initiator, polymerizing the monomer by stirring and heating the same and depositing a resin layer on the surface of the metallic pigment at least provided with the metallic particles can be preferably employed with reference to the case where the metallic particles are formed by electroless plating. Polymerization is desirably performed in a nonoxodizing atmosphere such as inert gas of nitrogen or argon, for example. If an oxidizing atmosphere is employed, radicals contributing to polymerization easily disappear and polymerization efficiency for the monomer tends to lower. The proper reaction temperature is 50 to 150° C., more preferably 70 to 100° C. Polymerization efficiency is excellent if the reaction temperature is at least 50° C., while excessive evaporation of the solvent is prevented preferably in consideration of the working environment and safety if the temperature is not more than 150° C.

A hydrocarbon-based solvent is particularly preferable as the aforementioned nonpolar solvent employed as a solvent for dispersion. A solvent such as mineral spirit, petroleum benzine, solvent naphtha, isoparaffin, normal paraffin, benzene, toluene xylene, cyclohexane, hexane, heptane, octane, chlorobenzene, trichlorobenzene, perchlorethylene, trichlorethylene or the like can be preferably illustrated as a preferable example of the nonpolar solvent. When employing the nonpolar solvent as the solvent for dispersion, deposition efficiency of the resin layer is excellent, and the outermost layer can be easily covered with a sufficient quantity of resin.

While the material for the covering resin layer is not particularly limited, a copolymer synthesized from at least two types of monomers including a reactive monomer having a carboxyl group and/or a phosphoric acid group and at least trifunctional multifunctional acrylic ester monomer and/or a polymerizable monomer having a benzene nucleus can be illustrated, for example.

The following substances are illustrated as examples of the reactive monomer having a carboxyl group and/or a phosphoric acid group. The content of the reactive monomer having a carboxyl group and/or a phosphoric acid group is preferably set in the range of 0.1 to 10 mass %, more preferably in the range of 0.5 to 5 mass % of the charged monomer component. If the content is out of this range, excellent film chemical resistance tends to be hard to attain.

As the examples of the reactive monomer having a carboxyl group and/or a phosphoric acid group, acrylic acid, methacrylic acid, malefic acid, crotonic acid, itaconic acid, fumaric acid, 2-methacryloyloxyethyl acid phosphate, di-2-methacryloyloxyethyl acid phosphate, tri-2-methacryloyloxyethyl acid phosphate, 2-acryloyloxyethyl acid phosphate di-2-acryloyloxyethyl acid phosphate, tri-2-acryloyloxyethyl acid phosphate, diphenyl-2-methacryloyloxyethyl acid phosphate, diphenyl-2-acryloyloxyethyl acid phosphate, dibutyl-2-methacryloyloxyethyl acid phosphate, dibutyl-2-acryloyoxyethyl acid phosphate, dioctyl-2-methacryloyloxyethyl acid phosphate, dioctyl-2-acryloyloxyethyl acid phosphate, 2-methacryloyloxypropyl acid phosphate, bis(2-chloroethyl) vinyl phosphonate, diallyldibutyl phosphonosuccinate and the like can be listed.

The following substances are illustrated as examples of at least trifunctional multifunctional acrylic acid ester monomer. The content of the multifunctional acrylic acid ester monomer is preferably set in the range of 30 to 90 mass %, more preferably in the range of 40 to 80 mass % of the charged monomer component. If the content is out of this range, excellent film chemical resistance tends to be hard to attain.

As the examples of at least trifunctional multifunctional acrylic acid ester monomer, trimethylol propane triacrylate, trimethylol propane trimethacrylate, tetramethylol propane triacrylate, tetramethylol propane tetraacrylate, tetramethylol propane trimethacrylate, tetramethylol propane tetramethacrylate, pentaerythritol triacrylate, pentaerythritol tetraacrylate, dipentaerythritot hexaacrylate, dirtimethylol propane tetraacrylate and the like can be listed.

This multifiunctional acrylic acid ester monomer has effects of contributing to three-dimensional crosslinking of the resin and insolubilizing the covering resin layer with respect to the organic solvent and water.

The following substances are illustrated as examples of the polymerizable monomer having a benzene nucleus. The content of the polymerizable monomer having a benzene nucleus is preferably set in the range of 5 to 50 mass %, more preferably in the range of 10 to 30 mass % of the charged monomer component. If the content is out of this range, excellent film chemical resistance tends to be hard to attain.

Styrene, α-methylstyrene, vinyltoluene, divinylbenzene, phenylvinyl ketone, phenylvinyl ether, divinylbenzene monoxide phenoxyethyl acrylate, phenoxy-polyethylene glycol acrylate, 2-hydroxy-3-phenoxypropyl acrylate and the like can be listed as the examples of the polymerizable monomer having a benzene nucleus.

This polymerizable monomer having a benzene nucleus is so copolymerized that a barrier effect of the covering resin layer against chemicals is improved and high chemical resistance is attained when the colored metallic pigment according to the present invention is worked into a film.

In the colored metallic pigment according to the present invention, the quantity of the covering resin layer is preferably set in the range of 1 to 100 parts by mass, more preferably 5 to 50 parts by mass with respect to 100 parts by mass of the metallic pigment. Excellent chemical resistance is attained if the quantity of the covering resin layer is at least 1 part by mass, while luster of the colored metallic pigment is hard to damage if the quantity is not more than 100 parts by mass.

The covering resin layer can be synthesized from the aforementioned monomer and the polymerization initiator. Peroxides such as benzoyl peroxide, lauroyl peroxide, isobutyl peroxide and methyl ethyl ketone peroxide and an azo compound such as azobis isobutylonitrile can be preferably illustrated as examples of the polymerization initiator.

The content of the polymerization initiator is preferably at least 0.1 parts by mass, more preferably at least 0.5 parts by mass in particular, with respect to 100 parts by mass of the charged monomer component. This content is preferably not more than 10 parts by mass, more preferably not more than 8 parts by mass in particular, with respect to 100 parts by mass of the charged monomer component. If the content is at least 0.1 parts by mass, polymerization excellently progresses and a film of an expected quantity can be easily formed. While adsorption of the formed polymer to the metallic pigment cannot follow, viscosity of the overall system is abruptly increased due to formation of free polymer particles and aggregation tends to easily result if polymerization abruptly progresses, abrupt progress of polymerization is prevented if the content is not more than 10 parts by mass, whereby the aforementioned inconvenience hardly takes place.

While the main structure of the colored metallic pigment according to the present invention has been described, the metal layer and the metallic particles may simply be formed in direct contact with each other in this colored metallic pigment, and a layer or a granular substance may further be formed in addition to the aforementioned ones, in a range not damaging the effects of the present invention.

<Coating Composition>

The present invention also relates to a coating composition obtained by blending the aforementioned colored metallic pigment into paint or ink. The coating composition according to the present invention includes paint and a film thereof, or ink and a print thereof, for example. Both of organic solvent type and water-based materials can be employed as the paint and the ink, it is important to improve light resistance and weather resistance in water-based paint or water-based ink, and hence the colored metallic pigment according to the present invention is effectively blended into water-based paint or water-based ink in particular.

The content of the colored metallic pigment in the coating composition is preferably set in the range of 0.1 to 30 mass % of the coating composition. A decorative effect such as a metallic effect is excellent if the content is at least 0.1 mass %, while weather resistance, corrosion resistance, mechanical strength etc. of the coating composition are excellent if the content is not more than 30 mass %. The content of the colored metallic pigment in the coating composition is more preferably set in the range of 1 to 20 mass % of the coating composition.

The coating composition is obtained by properly blending coating resin into the colored metallic pigment according to the present invention. Acrylic resin, alkyd resin, polyester resin, polyurethane resin, polyvinyl acetate resin, nitrocellulose resin, fluororesin or the like can be illustrated as the coating resin.

For the coating composition according to the present invention, another colored pigment or an extender pigment or a dyestuff may be employed in addition to the colored metallic pigment and the coating resin. As the employed colored pigment, phthalocyanine, quinacridone, isoindolinone, perylene, azo lake, iron oxide, chrome yellow, carbon black, titanium oxide, pearl mica or the like can be illustrated.

Into the coating composition according to the present invention, water, an organic solvent, a interfacial active agent, a hardener, an ultraviolet absorber, a static eliminator, a thickener etc. can be properly blended as additives, in addition to the aforementioned components.

When forming a film with the coating composition according to the present invention, the film may be formed on a base coat layer or an intercoat layer formed by electrodeposition coating or the like, while a top coat layer may further be formed on the film prepared from the coating composition according to the present invention, <Cosmetic Preparation>

The present invention also relates to a cosmetic preparation obtained by blending the aforementioned colored metallic pigment. While a pearl pigment or an aluminum pigment is generally employed in order to supply luster and sheen to a cosmetic preparation, the pearl pigment is inferior in hiding power, and the aluminum pigment presents gray and hence no vivid hues can be obtained by blending a colored pigment. Further, the aluminum pigment so easily reacts with water that the same cannot be used for a cosmetic preparation containing water.

A cosmetic preparation having excellent hiding power and exhibiting vivid hues can be obtained by blending the colored metallic pigment according to the present invention. Further, the colored metallic pigment according to the present invention is a stable colored metallic pigment hardly reacting with water, whereby the colored metallic pigment according to the present invention can be preferably applied also to a cosmetic preparation containing water.

The type of the cosmetic preparation blended with the colored metallic pigment according to the present invention is not particularly limited, the following cosmetic preparations are listed as specific embodiments:

(Embodiments of Cosmetic Preparation Blended with Colored Metallic Pigment According to the Present Invention)

(1) The following ones are listed as the types of cosmetic preparations:

Makeup preparations (lipstick, foundation, rouge, eye shadow, nail enamel etc.), hair preparations (hair gel, hair wax, hair treatment, shampoo, hair manicure gel etc.) and basic preparations (vanishing cream etc.).

(2) The following substances are listed as components constituting the cosmetic preparation, in addition to the colored metallic pigment according to the present invention:

(Oil)

Oils and fats (olive oil, castor oil etc.), waxes (beeswax, carnauba wax, lanolin etc.), hydrocarbon oils (liquid paraffin, squalane, polybutene etc.), fatty esters (isopropyl myristate, cetyl 2-ethylhexanate, diusopropyl adipate, glyceryl trimyristate etc.), higher fatty acids (oleic acid, isostearic acid etc.), higher alcohols (isostearyl alcohol, oleyl alcohol etc.) and silicone oils (dimethyl polysiloxane, methylphenyl polysiloxane, octamethyl cyclotetrasiloxane etc.) and fluorine compounds (perfluoropolyethcr etc.).

(Others)

Interfacial active agent, humectant, polyvalent alcohol, water-soluble polymer, film former, water-insoluble polymer, polymer emulsion, powder, pigment, dyestuff, lake, lower alcohol, ultraviolet absorber, vitamins, antioxidant, anti-fungus agent, perfume, water etc.

(Content)

As a preferable content of the colored metallic pigment in the cosmetic preparation, the range of 0.1 to 99 mass % can be illustrated, and the range of 1 to 80 mass % can be more preferably illustrated.

(3) Method of Mixing Cosmetic Preparation

A general cosmetic preparation producing method can be applied without particular limitation. Disperser or roll milling is preferable as a dispersion method.

<Producing Step>

The colored metallic pigment according to the present invention can be produced along the following steps, for example: When the underlayer is formed between the metallic pigment and the amorphous silicon oxide film layer in the present invention, the underlayer is first formed on the surface of the metallic pigment. Typically, a method stirring or kneading the metallic pigment and a solution containing a molybdenum compound and/or a phosphorus compound in a slurry state or a paste state, forming a hydrate film comprising molybdenum and/or phosphorus on the surface of the metallic pigment and thereafter forming an underlayer by heating or the like can be employed.

As the method of forming the surface modification layer in the case where the surface modification layer is formed on the surface of the metallic pigment, a method forming a hydrate film comprising the metallic element constituting the metallic pigment on the surface of the metallic pigment by stirring or kneading the metallic pigment and a solution containing hydrogen peroxide in a slurry state or a paste state and thereafter converting the hydrate film to an oxide film by heating or the like can be employed.

Then, the amorphous silicon oxide film layer is formed on the underlayer or the surface modification layer (amorphous silicon oxide film layer forming step). The amorphous silicon oxide film layer is formed on the surface of the metallic pigment by hydrolyzing an organic silicon compound in a solvent mainly composed of a hydrophilic solvent for depositing amorphous silicon oxide. For example, methyl alcohol, ethyl alcohol, isopropyl alcohol, n-propyl alcohol, t-butyl alcohol, n-butyl alcohol, isobutyl alcohol, ethyl cellosolve, butyl cellosolve, propylene glycol monobutyl ether, dipropylene glycol monomethyl ether, propylene glycol monopropyl ether, acetone or the like can be employed as the hydrophilic solvent. When employing alcohol as the hydrophilic solvent, the amorphous silicon oxide film layer is formed by forming alkoxy silicate on the surface of the metallic pigment and hydrolyzing and dehydrating/condensing the same. Acid or base is preferably employed as the catalyst for the aforementioned hydrolysis.

Then, the metal layer is formed on the surface of the metallic pigment covered with the amorphous silicon oxide film layer by the aforementioned method (metal layer forming step). The metal layer can be formed as a prestep for a metallic particle forming step described later. In other words, the metal layer is formed on the surface of the metallic pigment provided with the amorphous silicon oxide film layer by a method hydrolytically depositing metal alkoxide comprising at least one metal selected from Sn, Pd, Pt and Au, for example, as a metal species capable of forming an active site for depositing the metallic particles in the metallic particle forming step which is an afterstep by a sol-gel process or a method adding alkali to a metallic salt solution containing this metal and netralizing/depositing the same.

Then, the metallic particles are formed on the surface of the metal layer as homogeneous nanoparticulate matter by electroless plating or the like (metallic particle forming step). The electroless plating can be performed by a method slurrying the metallic pigment provided with the metal layer with water serving as a dispersion medium and thereafter adding an electroless plating solution, for example. The electroless plating solution typically at least contains a metal source mainly employed for forming the metallic particles, a reducing agent and a complexing agent.

Water-soluble metallic salt comprising any one of Al, Ti, Cr, Fe, Co, Ni, Cu, Zn, Ru, Rh, Rd, Ag, Sn, Pt and Au can be used as the metal source. Nitrate, nitrite, sulfate, oxalate, carbonate, chloride, acetate, lactate, sulfamate, fluoride, iodide, cyanide or the like can be used as the water-soluble salt.

Hypophosphorous acid, formaldehyde, boron hydride, dimethyl amineborane, trimethyl amineborane, hydrazine, glucose, tartaric acid or alkaline metal salt thereof can be used as the reducing agent.

Carboxylic acid such as succinic acid, oxycarboxylic acid such as citric acid or tartaric acid, organic acid such as glycine, EDTA or aminoacetic acid, or alkaline metal salt or ammonium salt of such acid can be used as the complexing agent. The metallic particles can be stably formed by employing the complexing agent.

The process for producing a colored metallic pigment according to the present invention preferably further includes a corrosion inhibiting layer forming step of forming a corrosion inhibiting layer on the metallic particles. While the method of forrruing the corrosion inhibiting layer is not particularly limited, a method of forming the corrosion inhibiting layer by adding a corrosion inhibitor to a suspension of a slurry state or a paste state prepared by suspending the metallic pigment at least provided with the amorphous silicon oxide film layer and the metallic particles in a hydrophilic solvent and stirring or kneading the same thereby bonding the corrosion inhibitor to the surface of the aforementioned metallic pigment can be employed, for example.

In the present invention, a weather-resistant coating layer forming step of forming a weather-resistant coating layer is preferably provided after the metallic particle forming step. When the weather-resistant coating layer comprises aluminum and/or silicon, a weather-resistant coating layer consisting of a single film or a mixture film of at least any one of an oxide, a hydroxide and a hydrate can be formed by stirring or kneading the metallic pigment at least provided with the metallic particles and a solution containing aluminum and/or silicon in a slurry state or a paste state for forming a hydrate film and thereafter heating the same, as hereinabove described. When the weather-resistant coating layer comprises cerium, a weather-resistant coating layer consisting of a single film or a mixture film of at least any one of an oxide, a hydroxide and a hydrate can be formed by adding the metallic pigment at least provided with the metallic particles into a solution in which cerium acetate, cerium nitrate, cerium alkoxide, cerium sol or the like is dissolved or dispersed and heating/stirring or kneading the same while keeping a basic atmosphere.

When the aforementioned weather-resistant coating layer is formed, a coupling treatment step is further preferably combined. The coupling treatment is performed by a method stirring or kneading the metallic pigment provided with the metallic particles and a solution containing aluminum and/or silicon in a slurry state or a paste state and thereafter adding a coupling agent if the weather-resistant coating layer comprises aluminum and/or silicon, or by a method adding the metallic pigment provided with the metallic particles to a solution or a dispersion of a cerium compound, heating/stirring or kneading the same while keeping a basic atmosphere and thereafter adding a coupling agent if the weather-resistant coating layer comprises cerium, for example. A method slurrying the metallic pigment provided with the weather-resistant coating layer by dispersing the same in a solvent such as isopropyl alcohol and adding a coupling agent to this slurry can also be employed.

The colored metallic pigment according to the present invention can be prepared by the aforementioned process. Further, the coating composition according to the present invention can be prepared by mixing the obtained colored metallic pigment with coating resin and another colored pigment, an extender pigment, a dyestuff, an additive etc. if necessary by a well-known method. In addition, the cosmetic preparation according to the present invention can be prepared by mixing the obtained colored metallic pigment with other components and dispersing the same by a well-known method employing disperser or roll milling.

EXAMPLES

While the present invention is now described in more detail with reference to Examples, the present invention is not restricted to these.

Example 1

A solution obtained by adding 0.3 g of metal molybdenum powder little by little to 3 g of hydrogen peroxide water containing 30 mass % of hydrogen peroxide and reacting the same was dissolved in 500 g of isopropyl alcohol (hereinafter abbreviated as IPA), a commercially available aluminum pigment (5422NS by Toyo Aluminum Kabushiki Kaisha—solid content: 75 mass %, average particle diameter: 19 Am, average thickness: 1 μm) was added by 40 g (i.e., 30 g as aluminum content) as a metallic pigment, and the materials were stirred and mixed at 75° C. for 1 hour, for obtaining slurry.

Thereafter ammonia water and 80 g of water were added to the aforementioned slurry, for adjusting the pH of the slurry to 10.0. A substance prepared by dissolving 40 g of tetraethoxysilane into 40 g of TPA was gradually dropped into the pH-adjusted slurry, and the materials were further stirred/mixed at 75° C. for 2 hours. Thereafter the slurry was solid-liquid separated through a filter and an amorphous silicon oxide film layer was formed on the surface of the metallic pigment (amorphous silicon oxide film layer forming step), thereby preparing a silica coat aluminum pigment.

10 g of the obtained silica coat aluminum pigment was dispersed in 300 g of an aqueous solution containing 40 g of tin chloride and 2 g of hydrochloric acid at 30° C. for 1 hour, solid-liquid separated again and cleaned with water, and a metal layer was formed on the surface of the silica coat aluminum pigment (metal layer forming step), for preparing a metal layer-covered aluminum pigment.

The obtained metal layer-covered aluminum pigment was dispersed in 800 g of an electroless silver plating solution containing 3 g of silver nitrate, 2 g of formaldehyde and 10 g of ammonia water and held at 30° C. for 1 hour for forming metallic particles on the surface of the metal layer (metallic particle forming step), thereby obtaining a metallic particle-bonded aluminum pigment. A blue colored aluminum pigment corresponding to the colored metallic pigment according to the present invention was obtained by solid-liquid separating and drying the obtained metallic particle-bonded aluminum pigment. When visually observed, this colored aluminum pigment presented interference colors changing from bluish-purple to dark brown depending on the angles of observation, and had excellent metallic effect.

Example 2

10 g of a silica coat aluminum pigment obtained through an amorphous silicon oxide film layer forming step similar to that in Example 1 was dispersed in 500 g of an aqueous solution containing 50 g of tin fluoride at 40° C. for 30 minutes for forming a metal layer on the surface of an amorphous silicon oxide film layer (metal layer forming step), solid-liquid separated again and cleaned with water, thereafter dispersed in 900 g of an electroless silver plating solution containing 3 g of silver nitrate, 40 g of glucose and 20 g of ammonia water and held at 40° C. for 10 minutes for forming metallic particles on the surface of the metal layer (metallic particle forming step), thereby obtaining a metallic particle-bonded aluminum pigment. A blue colored aluminum pigment corresponding to the colored metallic pigment according to the present invention was obtained by solid-liquid separating and drying the obtained metallic particle-bonded aluminum pigment. When visually observed, this colored aluminum pigment presented interference colors changing from blue to dark blue depending on the angles of observation, and had excellent metallic effect.

Example 3

10 g of a silica coat aluminum pigment obtained through an amorphous silicon oxide film layer forming step similar to that in Example 1 was dispersed in 400 g of an aqueous solution containing 30 g of sodium stannate at 50° C. for 50 minutes for forming a metal layer on the surface of an amorphous silicon oxide film layer (metal layer forming step), solid-liquid separated again and cleaned with water, thereafter dispersed in 200 g of an electroless silver plating solution containing 3 g of silver nitrate, 15 g of sodium potassium tartarate and 15 g of ammonia water and held at 35° C. for 40 minutes for forming metallic particles on the surface of the metal layer (metallic particle forming step), thereby obtaining a metallic particle-bonded aluminum pigment. A blue colored aluminum pigment corresponding to the colored metallic pigment according to the present invention was obtained by solid-liquid separating and drying the obtained metallic particle-bonded aluminum pigment. When visually observed, this colored aluminum pigment presented interference colors changing from bluish-purple to dark brown depending on the angles of observation, and had excellent metallic effect.

Example 4

10 g of a silica coat aluminum pigment obtained through an amorphous silicon oxide film layer forming step similar to that in Example 1 was dispersed in 200 g of an aqueous solution containing 40 g of tin chloride, 5 g of palladium chloride and 20 g of hydrochloric acid at 30° C. for 1 hour for forming a metal layer on the surface of an amorphous silicon oxide film layer (metal layer forming step), solid-liquid separated again and cleaned with 5% sulfuric acid, thereafter dispersed in 500 g of an electroless nickel plating solution containing 10 g of nickel sulfate, 5 g of sodium hypophosphite and 5 g of sodium citrate and held at 80° C. for 1 hour for forming metallic particles on the surface of the metal layer (metallic particle forming step), thereby obtaining a metallic particle-bonded aluminum pigment. A blue colored aluminum pigment corresponding to the colored metallic pigment according to the present invention was obtained by solid-liquid separating and drying the obtained metallic particle-bonded aluminum pigment. When visually observed, this colored aluminum pigment presented interference colors changing from pale blue to dark blue depending on the angles of observation, and had excellent metallic effect.

Example 5

10 g of a silica coat aluminum pigment obtained through an amorphous silicon oxide film layer forming step similar to that in Example 1 was dispersed in 300 g of an aqueous solution containing 50 g of tin chloride, 1 g of palladium chloride and 30 g of hydrochloric acid at 40° C. for 30 minutes for forming a metal layer on the surface of an amorphous silicon oxide film layer (metal layer forming step), solid-liquid separated again and cleaned with 1% hydrochloric acid, thereafter dispersed in 500 g of an electroless copper plating solution containing 5 g of copper sulfate, 2 g of formaldehyde and 15 g of EDTA-2Na and held at 60° C. for 1 hour for forming metallic particles on the surface of the metal layer (metallic particle forming step), thereby obtaining a metallic particle-bonded aluminum pigment. A blue colored aluminum pigment corresponding to the colored metallic pigment according to the present invention was obtained by solid-liquid separating and drying the obtained metallic particle-bonded aluminum pigment. When visually observed, this colored aluminum pigment presented interference colors changing from pale blue-green to dark blue-green depending on the angles of observation, and had excellent metallic effect.

Example 6

5 g of tetraethoysilane and 15 g of an aqueous solution of 10 mass % of urea were added to slurry prepared by dispersing 30 g of the colored metallic pigment obtained in Example 1 in 200 g of IPA and stirred/mixed at 75° C. for 5 hours for reacting the same (weather-resistant coating layer forming step). This slurry was filtrated, for obtaining a weather-resistant coating layer-covered aluminum pigment having a solid content of 60 mass %. Further, 2 g of γ-aminopropyl triethoxysilane was added to slurry prepared by dispersing 30 g of this weather-resistant coating layer-covered aluminum pigment in 400 g of IPA and stirred/mixed at 75° C. for 1 hour for reacting the same (coupling treatment step). This slurry was filtrated, for obtaining a colored aluminum pigment corresponding to the colored metallic pigment according to the present invention having a solid content of 60 mass %. The obtained colored aluminum pigment presented hues similar to those of Example 1.

Example 7

A weather-resistant coating layer forming step similar to that in Example 6 was carried out on 30 g of the colored aluminum pigment obtained in Example 1, 30 g of the obtained weather-resistant coating layer-covered aluminum pigment was filled into a separable flask of 1 liter with addition of 180 g of mineral spirit and stirred while introducing nitrogen gas, and the temperature in the system was increased to 80° C. Then, 0.06 g of acrylic acid, 1.2 g of epoxidized polybutadiene, 1.5 g of trimethytolpropane triacrylate, 0.54 g of divinylbenzene and 0.23 g of azobisisobutylonitrile were added and polymerized at 80° C. for 6 hours (covering resin layer forming step). After completion of polymerization, this slurry was filtrated, for obtaining a colored aluminum pigment corresponding to the colored metallic pigment according to the present invention having a solid content of 60 mass %. The obtained colored aluminum pigment presented hues similar to those of Example 1.

Example 8

A weather-resistant coating layer forming step similar to that in Example 6 was carried out on 30 g of the colored aluminum pigment obtained in Example 2, for obtaining a colored aluminum pigment corresponding to the colored metallic pigment according to the present invention having a solid content of 60 mass %. The obtained colored aluminum pigment presented hues similar to those of Example 2.

Example 9

A weather-resistant coating layer forming step similar to that in Example 6 was carried out on 30 g of the colored aluminum pigment obtained in Example 3, for obtaining a colored aluminum pigment corresponding to the colored metallic pigment according to the present invention having a solid content of 60 mass %. The obtained colored aluminum pigment presented hues similar to those of Example 3.

Example 10

A weather-resistant coating layer forming step similar to that in Example 6 was carried out on 30 g of the colored aluminum pigment obtained in Example 5, for obtaining a colored aluminum pigment corresponding to the colored metallic pigment according to the present invention having a solid content of 60 mass %. The obtained colored aluminum pigment presented hues similar to those of Example 5.

Example 11

10 g of hydrogen peroxide water containing 30 mass % of hydrogen peroxide was dissolved in 500 g of IPA, 40 g of an aluminum pigment (5422NS by Toyo Aluminum Kabushiki Kaisha) was further added as a metallic pigment, and stirred/mixed at 75° C. for 1 hour for obtaining slurry (surface modification layer forming step).

An amorphous silicon oxide film layer forming step and an electroless plating step were carried out similarly to Example 1. The obtained colored aluminum pigment was solid-liquid separated and dried, thereby obtaining a colored aluminum pigment presenting hues similar to those in Example 1.

Example 12

0.1 g of benzotriazole, 1 g of methyl alcohol and 0.1 g of sodium hydroxide were added to slurry prepared by dispersing 30 g of the colored aluminum pigment obtained in Example 1 in water and dispersed at 30° C. for 10 minutes for forming a corrosion inhibiting layer on the surfaces of the metallic particles (corrosion inhibiting layer forming step), thereby obtaining a colored aluminum pigment. The obtained colored aluminum pigment was solid-liquid separated and dried, thereby obtaining a colored aluminum pigment presenting hues similar to those in Example 1.

Example 13

A weather-resistant coating layer forming step similar to that in Example 6 was carried out on 30 g of the colored aluminum pigment obtained in Example 12, for obtaining a colored aluminum pigment corresponding to the colored metallic pigment according to the present invention having a solid content of 60 mass %. The obtained colored aluminum pigment presented hues similar to those in Example 1.

Comparative Example 1

10 g of a silica coat aluminum pigment obtained through an amorphous silicon oxide film layer forming step similar to that in Example 1 was dispersed in 800 g of an electroless silver plating solution containing 3 g of silver nitrate, 2 g of formaldehyde and 10 g of ammonia water and held at 30° C. for 1 hour. The obtained flakes were solid-liquid separated and dried, to obtain an aluminum pigment presenting pale blue. When this aluminum pigment was visually observed, color floppiness was weak, and chroma was low.

Comparative Example 2

10 g of a silica coat aluminum pigment obtained through an amorphous silicon oxide film layer forming step similar to that in Example 1 was disperse in 500 g of an electroless nickel plating solution containing 10 g of nickel sulfate, 5 g of sodium hypophosphite and 5 g of sodium citrate and held at 80° C. for 1 hour. The obtained flakes were solid-liquid separated and dried, to obtain an aluminum pigment presenting the matrix metal color. When this aluminum pigment was visually observed, neither color floppiness nor chroma was developed.

Comparative Example 3

10 g of a silica coat aluminum pigment obtained through an amorphous silicon oxide film layer forming step similar to that in Example 1 was disperse in 500 g of an electroless copper plating solution containing 5 g of copper sulfate, 2 g of formaldehyde and 15 g of EDTA-4Na and held at 60° C. for 1 hour. The obtained flakes were solid-liquid separated and dried, to obtain an aluminum pigment presenting the matrix metal color. When this aluminum pigment was visually observed, neither color floppiness nor chroma was developed.

Table 1 shows hues and interference effects of the colored aluminum pigments and the aluminum pigments obtained in the respective Examples and the respective comparative examples.

TABLE 1

|  | Raw Material for Metal Layer | Raw Material for Metallic Particles | Hue | Interference Effect (Note 1) |
|---|---|---|---|---|
| Example 1 | Tin Chloride | Silver Nitrate | Bluish-Purple - Dark Brown | A |
| Example 2 | Tin Fluoride | Silver Nitrate | Blue - Dark Blue | A |
| Example 3 | Sodium Stannate | Silver Nitrate | Bluish-Purple - Dark Brown | A |
| Example 4 | Tin Chloride Palladium Chloride | Nickel Sulfate | Pale Blue - Dark Blue | A |
| Example 5 | Tin Chloride Palladium Chloride | Copper Sulfate | Pale Blue-Green - Dark Blue-Green | A |
| Comparative Example 1 | — | Silver Nitrate | Pale Bluish-Purple - Brown | B |
| Comparative Example 2 | — | Nickel Sulfate | Silver (Not Colored) | C |
| Comparative Example 3 | — | Copper Sulfate | Silver (Not Colored) | C |

Note 1)
A: having color floppiness B: slightly having color floppiness C: having no color floppiness As shown in Table 1, Examples 1 to 5 were excellent in both of hues and interference effects as compared with comparative examples i to 3. From these results, it is understood that the colored metallic pigment according to the present invention is supplied with vivid hues and a high interference effect due to the metallic layer and the metallic particles formed on this metallic layer.

<Weather Resistance Evaluation>

Each of the colored aluminum pigments obtained in Examples 2 and 4 and 6 to 13 and the aluminum pigment obtained in comparative example 1 was employed for preparing a coating composition (hereinafter referred to as a colored base coating composition) having the following composition, and the coating composition was applied to the surface of a steel plate obtained by performing polyester/melamine resin-based intercoating on a surface-treated steel sheet (prepared by performing zinc phosphate-based chemical conversion on a steel plate of JISG3310) to which cationic electrodeposition paint for an automobile was electrodeposited.

The aforementioned steel plate subjected to electrodeposition coating and intercoating was air-spray-coated with the colored base coating composition and a clear coating composition having the following composition in a two-coat one-bake system and baked at 140° C. for 30 minutes, for preparing a metallic film having a colored base coating layer and a clear coating layer. The thicknesses of the colored base coating layer and the clear coating layer after hardening/drying were 15 μm and 35 μm respectively.

| (Colored Base Coating Composition) | |
|---|---|
| colored aluminum pigment or aluminum pigment (solid content): | 10 parts by mass |
| thermosetting acrylic resin (solid content): | 80 parts by mass |
| butylated melamine resin (solid content): | 20 parts by mass |
| ethyl acetate: | 100 parts by mass |
| toluene: | 100 parts by mass |

-continued

| | |
|---|---|
| IPA: | 100 parts by mass |

(Clear Coating Composition)

| | |
|---|---|
| thermosetting acrylic resin (solid content): | 80 parts by mass |
| butylated melamine resin (solid content): | 20 parts by mass |
| ethyl acetate: | 50 parts by mass |
| toluene: | 50 parts by mass |
| IPA: | 50 parts by mass |

As to the weather resistance of the obtained coated plate, the degree of discoloration of the coated plate tested with a Supecrxenon accelerated weathering tester (Superxenon Weather Meter SX75 by Suga Test Instruments) for 1000 hours was evaluated as color difference (i.e., the square root of the sum of squares of the respective ones of L*, a* and b* values of the coated plate before and after the test: AE. no unit) of a color-difference meter ("CR300" by Minolta Co., Ltd.) according to JTS K5400-1990. Table 2 shows the results.

Weather resistance evaluation of Example 4 was particularly excellent conceivably because the raw material for the metallic particles was nickel sulfate and Ni which does not oxidize or sulfurize as easily as Ag or Cu was deposited as the metallic particles.

<Hue Change Evaluation>

Then, comparative evaluation was conducted as to hue changes in cases of forming and not forming metal layers. First, coating compositions were prepared by mixing the colored aluminum pigment obtained in Example 2 and the aluminum pigment obtained in comparative example 1 with coating resin respectively. Each coating composition was prepared by adding 5 parts by mass of the colored aluminum pigment or the aluminum pigment to 100 parts by mass of coating resin (Nippe Acryl Autoclear: by Nippon Paint Co., Ltd.) and stirring the same. Coated paper obtained by applying the prepared coating composition to art paper with an applicator of wet 225 μm and drying the same at the room temperature for at least 1 hour was color-measured.

TABLE 2

| | Raw Material for Metal Layer | Raw Material for Metallic Particles | Corrosion Inhibiting Layer | Weather-Resistant Coating Layer | Coupling Treatment | Resin Layer | Evaluation of Weather Resistance (ΔE) |
|---|---|---|---|---|---|---|---|
| Comparative Example 1 | — | Silver Nitrate | no | no | no | no | 9.8 |
| Example 2 | Tin Fluoride | Silver Nitrate | no | no | no | no | 12.5 |
| Example 4 | Tin Chloride Palladium Chloride | Nickel Sulfate | no | no | no | no | 0.5 |
| Example 6 | Tin Chloride | Silver Nitrate | no | yes | yes | no | 0.7 |
| Example 7 | Tin Chloride | Silver Nitrate | no | yes | no | yes | 0.5 |
| Example 8 | Identical to Example 2 | | no | yes | no | no | 0.9 |
| Example 9 | Identical to Example 3 | | no | yes | no | no | 0.8 |
| Example 10 | Identical to Example 5 | | no | yes | no | no | 1.5 |
| Example 11 | Identical to Example 1 | | no | no | no | no | 8.9 |
| Example 12 | Identical to Example 1 | | yes | no | no | no | 2.6 |
| Example 13 | Identical to Example 1 | | yes | yes | no | no | 0.3 |

In the coated plate according to Example 2 employing the colored aluminum pigment provided with neither weather-resistant coating layer nor covering resin layer among Examples 2, 4 and 6 to 13 each coated with the coating composition comprising the colored aluminum pigment corresponding to the colored metallic pigment according to the present invention, no effect of improving the weather resistance is attained also as compared with the coated plate according to comparative example 1 employing the aluminum pigment provided with neither metal layer, nor weather-resistant coating layer nor covering resin layer. In each of the coated plates according to Examples 6 to 10 employing the colored aluminum pigment provided with the weather-resistant coating layer, on the other hand, the result of weather resistance evaluation (ΔE) is remarkably excellent as compared with comparative example 1 and Example 2. From these results, it is understood that the effect of improving weather resistance can be attained by providing the weather-resistant coating layer.

Example 12 exhibited more excellent weather resistance than Example 11, and Example 13 exhibited further excellent weather resistance than Example 12. From these results, it is understood that the effect of improving weather resistance is attained by providing the corrosion inhibiting layer, and a particularly excellent effect of improving weather resistance is attained when combining the corrosion inhibiting layer and the weather-resistant coating layer with each other.

Hue evaluation was conducted by measuring brightness and chroma of the coated plate with a multiangular spectrocolorimeter X-Rite MA68II. Colorimetric values were expressed in the L*a*b* calorimetric system (CIE1976), and the color floppiness was particularly evaluated while noting changes of a*b* values. Further, the colored aluminum pigment according to Example 2 and the aluminum pigment according to comparative example 1 present bluely colors, and hence b* values were also noted. In colorimetry, light components deviating from regular reflected light by 15°, 25°, 45°, 75° and 110° with respect to incident light were detected. Table 3 shows measured values. Referring to Table 3, directions + and − of the b* values show yellow and blue respectively.

TABLE 3

| | 15° | 25° | 45° | 75° | 110° |
|---|---|---|---|---|---|
| Comparative Example 1 | −42.24 | −28.09 | −4.76 | 10.56 | 15.18 |
| Example 2 | −94.52 | −67.92 | −26.75 | −4.75 | 1.55 |

From the results shown in Table 3, bluely hues were larger at all colorimetric angles in Example 2 having the metal layer of Sn provided between the amorphous silicon oxide film layer and the metallic particles as compared with comparative example 1 provided with no metal layer. In Example 2, further, color floppiness was also more excellent as compared with comparative example 1. This is conceivably because the metallic particles were more finely deposited in a dense state due to the provision of the metal layer.

<Preparation of Cosmetic Preparation>

Various types of cosmetic preparations were prepared with the colored metallic pigment of Example 1 according to the following prescriptions, and compared with conventional commercially available cosmetic preparations:

Example 14

| Eye Shadow (Stick Type) | |
| --- | --- |
| (1) talc: | 5.0 parts by mass |
| (2) titanium dioxide: | 3.0 parts by mass |
| (3) colored metallic pigment: | 50.0 parts by mass |
| (4) carnauba wax: | 10.0 parts by mass |
| (5) solid paraffin: | 5.0 parts by mass |
| (6) lanolin derivative: | 5.0 parts by mass |
| (7) squalane: | 20.9 parts by mass |
| (8) sorbitan sesquioleate: | 1.0 part by mass |
| (9) perfume: | 0.1 parts by mass |

Example 15

| Hair Preparation (Hair Gel) | |
| --- | --- |
| (1) carboxyvinyl polymer: | 5.0 parts by mass |
| (2) ethyl alcohol: | 2.0 parts by mass |
| (3) PEG1500: | 1.0 part by mass |
| (4) aminomethyl propanol: | 1.5 parts by mass |
| (5) methylparaben: | 0.1 parts by mass |
| (6) colored metallic pigment: | 7.0 parts by mass |
| (7) refined water: | 83.4 parts by mass |

Example 16

| Nail Enamel | |
| --- | --- |
| (1) nitrocellulose (½ sec): | 6.5 parts by mass |
| (2) nitrocellulose (⅛ sec): | 11.0 parts by mass |
| (3) toluenesulfoneamide resin: | 12.5 parts by mass |
| (4) acetotributyl citrate: | 5.3 parts by mass |
| (5) camphor: | 1.0 part by mass |
| (6) n-butyl alcohol: | 0.5 parts by mass |
| (7) ethyl alcohol: | 4.5 parts by mass |
| (8) ethyl acetate: | 15.0 parts by mass |
| (9) butyl acetate: | 30.0 parts by mass |
| (10) colored metallic pigment: | 13.7 parts by mass |

In either case, a cosmetic preparation superior in hiding power and luster to the conventional cosmetic preparations while exhibiting vivid hues was obtained.

<Form Observation of Colored Aluminum Pigment and Aluminum Pigment>

Figure 2:
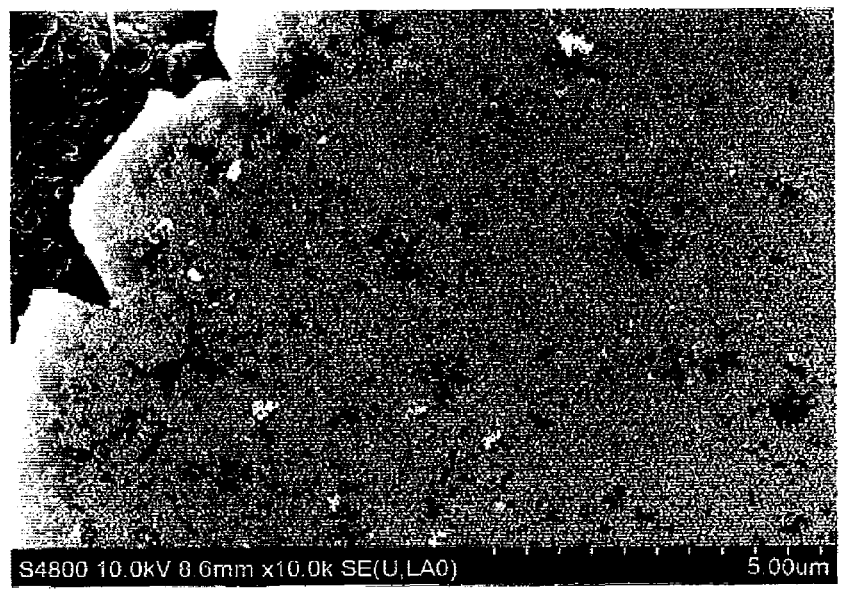
FIG. 2 shows the surface form of an aluminum pigment obtained in comparative example 1.
Figure 3:
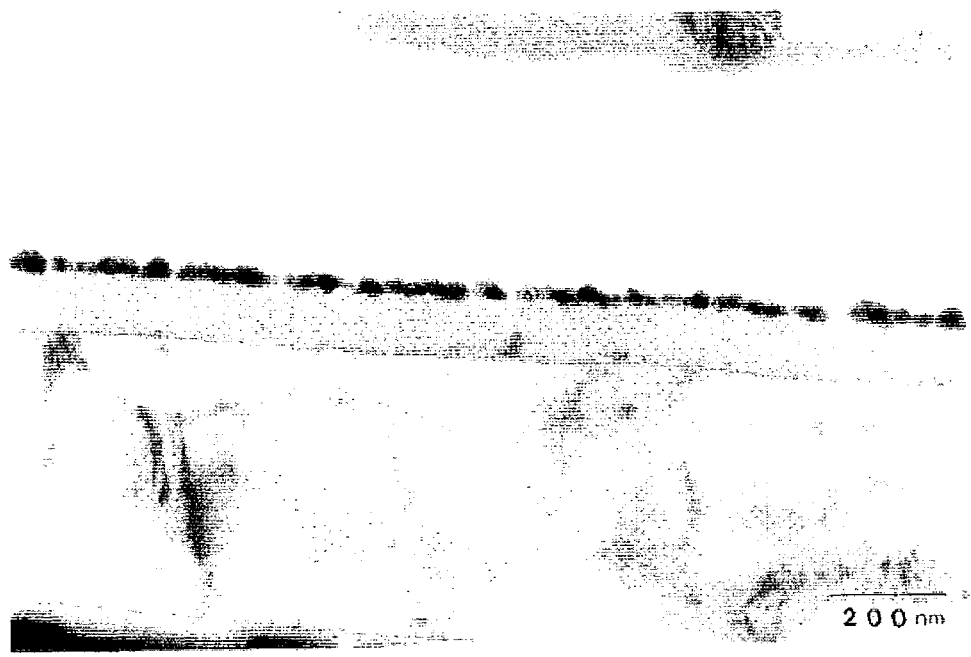
FIG. 3 shows the sectional form of the colored aluminum pigment obtained in Example 2.
Figure 4:
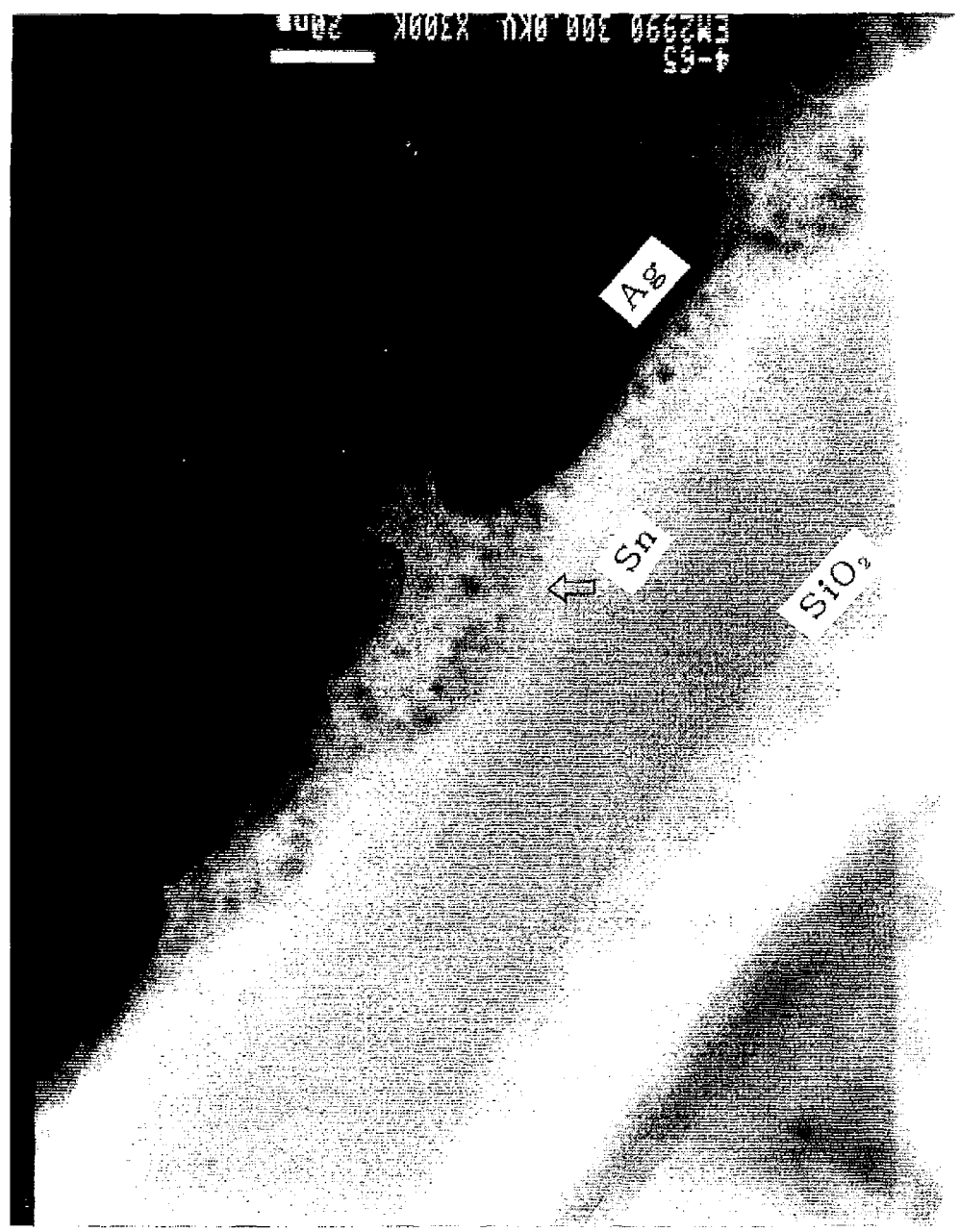
FIG. 4 shows the sectional form of the colored aluminum pigment obtained in Example 2

The surfaces of the colored aluminum pigment obtained in Example 2 and the aluminum pigment obtained in comparative example 1 were observed with a scanning electron microscope (FE-SEM). FIG. 1 shows the surface form of the colored aluminum pigment obtained in Example 2, and FIG. 2 shows the surface form of the aluminum pigment obtained in comparative example 1. Furthers sections of the colored aluminum pigment obtained in Example 2 and the metallic pigment immediately after the metal layer forming step in Example 2 were observed with the transmission electron microscope (TEM). FIGS. 3 and 4 show the sectional forms of the colored aluminum pigment obtained in Example 2.

As understood from the form shown in FIG. 1, the metallic particles are formed on the surface of the colored aluminum pigment obtained in Example 2 in independent granular states. Further, the metallic particles are relatively homogeneously deposited on the surface of the colored aluminum pigment. As understood from the form shown in FIG. 2, on the other hand, the metallic particles are aggregately deposited on the surface of the aluminum pigment obtained in comparative example 1 and the metallic particles are also deposited under the outermost metallic particles in a superposed manner, and hence the metallic particles are so layered that the surface of the aluminum pigment is covered with the metallic particles on the portions where the metallic particles are deposited. Further, the aluminum pigment obtained in comparative example 1 has a large number of portions where the metallic particles exfoliate in the range of the μm level.

In other words, no metal layer serving as an adsorption site for the metallic particles is formed between the amorphous silicon oxide film layer and the metallic particles in the aluminum pigment according to comparative example 1, and hence it is estimated that the deposited metallic particles are merely physically adsorbed on portions other than the surface of the amorphous silicon oxide film layer and adsorption between the metallic particles and the amorphous silicon oxide film layer is so weak that exfoliating portions resulted from mechanical sharing in the metallic particle forming step. Thus, it is conceivable that an interference effect by light passing through the metallic particles is not sufficiently attained but color floppiness is weakened and chroma is reduced in comparative example 1.

On the other hand, dense and fine metallic particles are deposited in Example 2, and this is estimated as an effect resulting from the metal layer, provided between the amorphous silicon oxide film layer and the metallic particles, serving as an adsorption site for the metallic particles. In the colored aluminum pigment according to Example 2, it is conceivable that light is scattered in the amorphous silicon oxide film layer by light reflected by the base metallic pigment and light reflected by the metallic particles while the light reflected by the metallic particles and the reflected light passing through the metallic particles interfere with each other, whereby high color floppiness and high chroma are supplied, and an excellent interference effect is developed.

When measured from the sectional form image shown in FIG. 3, the average particle diameter of Ag particles corresponding to the metallic particles formed in the present invention was 20 nm, and the thickness of the amorphous silicon oxide film layer was 100 nm. When measured from the sectional form image shown in FIG. 4, the thickness of an Sn layer corresponding to the metal layer formed in the present invention was about 20 to 30 nm. While it was not possible to clearly observe the metal layer due to the limit of sectional form observation in FIG. 3, the metal layer was clearly observed in FIG. 4. In other words, it is recognized that the colored aluminum pigment according to Example 2 is provided with the metal layer and the metallic particles.

The embodiment and Examples disclosed this time are to be considered as illustrative in all points and not restrictive. The range of the present invention is shown not by the above description but by the scope of claims for patent, and it is intended that all modifications within the meaning and range equivalent to the scope of claims for patent are included.

INDUSTRIAL APPLICABILITY

The colored metallic pigment according to the present invention advantageously has a variety of colors and varied interference colors while excellently maintaining light resistance, weather resistance and hiding power. A coating composition providing a coating film excellent in finished appearance can be formed by using the colored metallic pigment according to the present invention for various types of paint and ink. Further, a cosmetic preparation having excellent hiding power and capable of obtaining vivid hues can be formed by using the colored metallic pigment according to the present invention for the cosmetic preparation. This colored metallic pigment is preferably employed for water-based paint or ink in particular.

The invention claimed is:

1. A colored metallic pigment comprising at least a metallic pigment, an amorphous silicon oxide film layer provided on the surface of said metallic pigment, a metal layer provided on the surface of said amorphous silicon oxide film layer and metallic particles provided on the surface of said metal layer, wherein
said metallic particles are so provided as to directly cover part of said metal layer.

2. The colored metallic pigment according to claim 1, wherein
said metal layer comprises at least one element selected from Sn, Pd, Pt and Au.

3. The colored metallic pigment according to claim 1, wherein
said metallic particles comprise at least one element selected from Cu, Ni and Ag.

4. The colored metallic pigment according to claim 1, wherein
an underlayer is formed between said metallic pigment and said amorphous silicon oxide film layer, and
said underlayer comprises a single film or a mixture film of at least any one of an oxide, a hydroxide and a hydrate comprising molybdenum and/or phosphorus.

5. The colored metallic pigment according to claim 1, wherein
a surface modification layer comprising an oxide of the metallic element constituting said metallic pigment is formed on the surface of said metallic pigment.

6. The colored metallic pigment according to claim 1, wherein
the thickness of said amorphous silicon oxide film layer is in the range of 10 to 500 nm, and the average particle diameter of said metallic particles is not more than 50 nm.

7. The colored metallic pigment according to claim 1, wherein
a corrosion inhibiting layer comprising a corrosion inhibitor is formed on said metallic particles.

8. The colored metallic pigment according to claim 1, wherein
a weather-resistant coating layer is further formed on said metallic particles, and
said weather-resistant coating layer comprises a single film or a mixture film of at least any one of an oxide, a hydroxide and a hydrate comprising at least one element selected from aluminum, silicon and cerium.

9. The colored metallic pigment according to claim 1, wherein
a covering resin layer is further formed as the outermost layer.

10. A coating composition at least comprising the colored metallic pigment according to claim 1.

11. A cosmetic preparation at least comprising the colored metallic pigment according to claim 1.

12. A process for producing a colored metallic pigment, for obtaining the colored metallic pigment according to claim 1, at least comprising:
an amorphous silicon oxide film layer forming step of forming an amorphous silicon oxide film layer on the surface of a metallic pigment by hydrolyzing an organic silicon compound in a solvent mainly composed of a hydrophilic solvent for depositing amorphous silicon oxide;
a metal layer forming step of depositing a metal layer on the surface of said amorphous silicon oxide film layer; and
a metallic particle forming step of forming metallic particles on the surface of said metal layer by electroless plating.

13. The process for producing a colored metallic pigment according to claim 12, wherein
said metal layer comprises at least one element selected from Sn, Pd, Pt and Au.

14. The process for producing a colored metallic pigment according to claim 12, further comprising an underlayer forming step of performing pretreatment on the surface of said metallic pigment with inorganic acid comprising molybdenum and/or phosphorus for forming an underlayer comprising a single film or a mixture film of at least any one of an oxide, a hydroxide and a hydrate comprising said molybdenum and/or said phosphorus in advance of said amorphous silicon oxide film layer forming step.

15. The process for producing a colored metallic pigment according to claim 12, further comprising a surface modification layer forming step of forming a surface modification layer comprising an oxide of the metallic element constituting said metallic pigment by treating the surface of said metallic pigment with hydrogen peroxide in advance of said amorphous silicon oxide film layer forming step.

16. The process for producing a colored metallic pigment according to claim 12, further comprising a corrosion inhibiting layer forming step of forming a corrosion inhibiting layer comprising a corrosion inhibitor after said metallic particle forming step.

17. The process for producing a colored metallic pigment according to claim 12, further comprising:
a weather-resistant coating layer forming step of forming a weather-resistant coating layer comprising a single film or a mixture film of at least any one of an oxide, a hydroxide and a hydrate comprising at least one element selected from aluminum, silicon and cerium after said metallic particle forming step, and
a coupling treatment step of treating said weather-resistant coating layer with a coupling agent comprising silicon and/or titanium.

* * * * *